US012569644B2

(12) United States Patent
Patchin et al.

(10) Patent No.: US 12,569,644 B2
(45) Date of Patent: Mar. 10, 2026

(54) SYSTEMS AND METHODS FOR CATHETER RESTORATION

(71) Applicant: INNOVATIVE HEALTH, Scottsdale, AZ (US)

(72) Inventors: Roy Patchin, Scottsdale, AZ (US); Haydn Oleson, Peoria, AZ (US); Blessan C. Joseph, Chandler, AZ (US); Rafal Chudzik, Peoria, AZ (US)

(73) Assignee: INNOVATIVE HEALTH, Scottsdale, AZ (US)

( * ) Notice: Subject to any disclaimer, the term of this patent is extended or adjusted under 35 U.S.C. 154(b) by 0 days.

(21) Appl. No.: 18/436,093

(22) Filed: Feb. 8, 2024

(65) Prior Publication Data

US 2025/0256058 A1 Aug. 14, 2025

(51) Int. Cl.
| | |
|---|---|
| *A61M 25/00* | (2006.01) |
| *A61M 25/02* | (2006.01) |
| *B29C 67/00* | (2017.01) |
| *B29L 31/00* | (2006.01) |

(52) U.S. Cl.
CPC .......... *A61M 25/001* (2013.01); *A61M 25/02* (2013.01); *A61M 2205/3368* (2013.01); *B29C 67/0014* (2013.01); *B29L 2031/7542* (2013.01)

(58) Field of Classification Search
CPC ..... B29C 67/0014; B29C 53/20; B29C 53/84; B29L 2031/7542; A61M 25/0009–0015
See application file for complete search history.

(56) References Cited

U.S. PATENT DOCUMENTS

| | | | |
|---|---|---|---|
| 9,868,238 B1* | 1/2018 | Scopton ................. | B29C 45/78 |
| 2007/0215268 A1* | 9/2007 | Pingleton ............ | A61M 25/005 |
| | | | 156/169 |
| 2014/0251536 A1* | 9/2014 | Wrolstad ............... | B29C 57/00 |
| | | | 156/294 |
| 2022/0032002 A1* | 2/2022 | Baxter ................. | B29C 64/245 |
| 2022/0401692 A1* | 12/2022 | Allmendinger ....... | A61M 25/00 |

OTHER PUBLICATIONS

Desktop Wire Mandrel Straightening Machine youtube video available as of Jan. 26, 2022, <https://www.youtube.com/watch?v=9PLAg5VvwOo> (Year: 2022).*
Desktop Wire Mandrel Straightening Machine youtube video available as of Jan. 26, 2022, <https://www.youtube.com/watch?v=9PLAg5VvwOo> (Year: 2022) (Year: 2022).*
Commercially available wire straightening machine from AliExpress, English translation retrieved on Nov. 25, 2024. (Year: 2024).*

* cited by examiner

Primary Examiner — Susan D Leong
Assistant Examiner — Vipul Malik
(74) *Attorney, Agent, or Firm* — POLSINELLI PC

(57) ABSTRACT

A system for removing kinks in a catheter and/or reforming a catheter of a medical device is provided. The system can include at least one clamp, a heat device, and a pair of rolling wheels. In at least one example, the at least one clamp can be operable to secure the catheter. In some examples, the heat device can be operable to provide heat to the catheter. In some examples, the pair of rolling wheels can be operable to receive the catheter of the medical device therebetween such that when the catheter is moved along a longitudinal axis between the pair of rolling wheels, the pair of rolling wheels reforms the catheter.

22 Claims, 13 Drawing Sheets

400

402

B

404

406

500

518

506

109

512

502

201

514

508

516

504

516

201

520

902

Choose a Recipe
Warm Up
← Start →

Finished !
Do You Want to Run
this Recipe Again?
No    Yes

Viewflex
Is Device Positioned
Correctly ?
Back    Start

WARNING
HEAT STARTING IN
3

WARNING
8
HEAT IN USE

Begin Rolling
10
STILL HOT

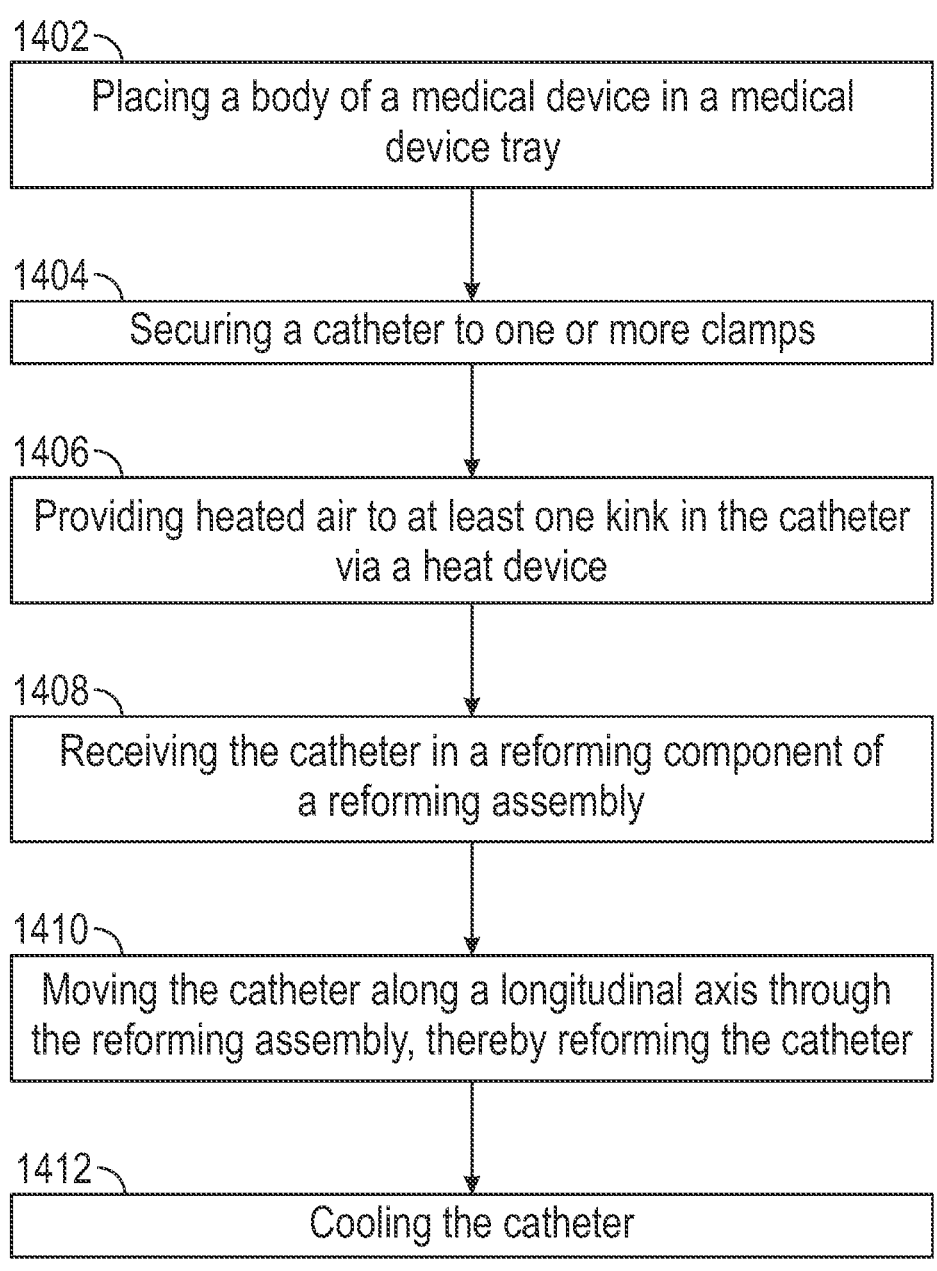

1402—
| Placing a body of a medical device in a medical device tray |
| --- |

1404—
| Securing a catheter to one or more clamps |
| --- |

1406—
| Providing heated air to at least one kink in the catheter via a heat device |
| --- |

1408—
| Receiving the catheter in a reforming component of a reforming assembly |
| --- |

1410—
| Moving the catheter along a longitudinal axis through the reforming assembly, thereby reforming the catheter |
| --- |

1412—
| Cooling the catheter |
| --- |

FIG. 14

SYSTEMS AND METHODS FOR CATHETER RESTORATION

FIELD

The present disclosure is directed to systems and methods for reforming a catheter of a medical device.

BACKGROUND

In many instances, reprocessing medical devices can provide cost efficient alternatives to newly manufactured medical devices. For example, devices that are reprocessed can have the same functionality as an originally manufactured medical device at a fraction of the cost. However, significant care must be taken when reprocessing medical devices to ensure that the reprocessed device has the same functionality as the originally manufactured device.

For medical devices with catheters, the catheter can become deformed during use or during post-use storage. In other examples, the catheter could be deformed due to a manufacturing defect, improper handling, or improper use. Therefore, there is a need for a catheter restoration system and methods for reforming catheters that have kinks and/or other defects in order to fully reprocess the catheters.

SUMMARY

Provided herein is a system for removing kinks in a catheter of a medical device and/or reforming the catheter of the medical device. The system can include at least one clamp operable to secure the catheter, a heat device operable to provide heat to the catheter secured by the at least one clamp, and a reforming assembly. In at least one example, the reforming assembly can include a reforming component operable to receive the catheter of the medical device therein such that when the catheter is moved along a longitudinal axis through the reforming assembly, the reforming assembly reforms the catheter. In some examples, the system can further include a medical device tray operable to hold the medical device. In some examples, the reforming assembly includes a pair of rolling wheels. In some examples, the reforming component includes a groove formed along a circumference of each wheel of the pair of wheels. In some examples, the grooves are operable to contact an exterior surface of the catheter and reform the exterior surface of the catheter. In at least one example, at least one wheel of the pair of rolling wheels can have an adjustable vertical position. In at least one example, the system can include one or more additional pairs of rolling wheels.

In at least on example, the heat device is operable to provide heated air to the catheter at a temperature of about 55 degrees C. to about 170 degrees C. In some examples, the heated air is operable to soften the catheter of the medical device. In at least one example, the system can further include at least one guide rail. In some examples, the at least one clamp can be slidably coupled to the at least one guide rail. In some examples, the at least one clamp can include a first clamp and a second clamp.

In at least one example, the system can further include a processor and a display. In some examples, the processor can be configured to receive one or more inputs from an operator, display one or more instructions to the operator via the display, and cause the heat device to provide heated air to the catheter. In some examples, the one or more instructions can include one or more of choose recipe, cooling in progress, remove medical device, and confirm medical device restoration.

Further provided herein is a method for reforming a catheter of a medical device. The method can include placing a body of a medical device in a medical device tray, securing the catheter to one or more clamps, providing heated air to at least one kink in the catheter via a heat device, receiving the catheter in a reforming component of a reforming assembly, moving the catheter along a longitudinal axis through the reforming assembly, and cooling the catheter. In at least one example, providing heated air to the at least one kink in the catheter can soften a material of the catheter. In at least one example, moving the catheter along a longitudinal axis through the reforming assembly reforms the catheter. In at least one example, the heated air can have a temperature of about 55 degrees C. to about 170 degrees C. In some examples, the heated air is provided for about 5 seconds to about 20 seconds. In some examples, the method can further include inspecting the catheter. In some examples, the method can further include repeating the method if the catheter is not fully restored to a desired shape. In at least one example, the method can further include sterilizing the medical device. In at least one example, each wheel of the pair of wheels can have a groove for receiving the catheter. In at least one example, the reforming assembly includes a pair of rolling wheels. In some examples, the reforming component includes a groove formed along a circumference of each wheel of the pair of wheels.

BRIEF DESCRIPTION OF THE DRAWINGS

Details of one or more aspects of the subject matter described in this disclosure are set forth in the accompanying drawings and the description below. However, the accompanying drawings illustrate only some typical aspects of this disclosure and are therefore not to be considered limiting of its scope. Other features, aspects, and advantages will become apparent from the description, the drawings and the claims.

FIGS. 10A-10F illustrate various instructions, statuses, and warnings displayed on a display screen;

FIG. 14 illustrates a flow chart of a method for restoring kinks in a catheter and/or reforming a catheter.

DETAILED DESCRIPTION

Figure 1:
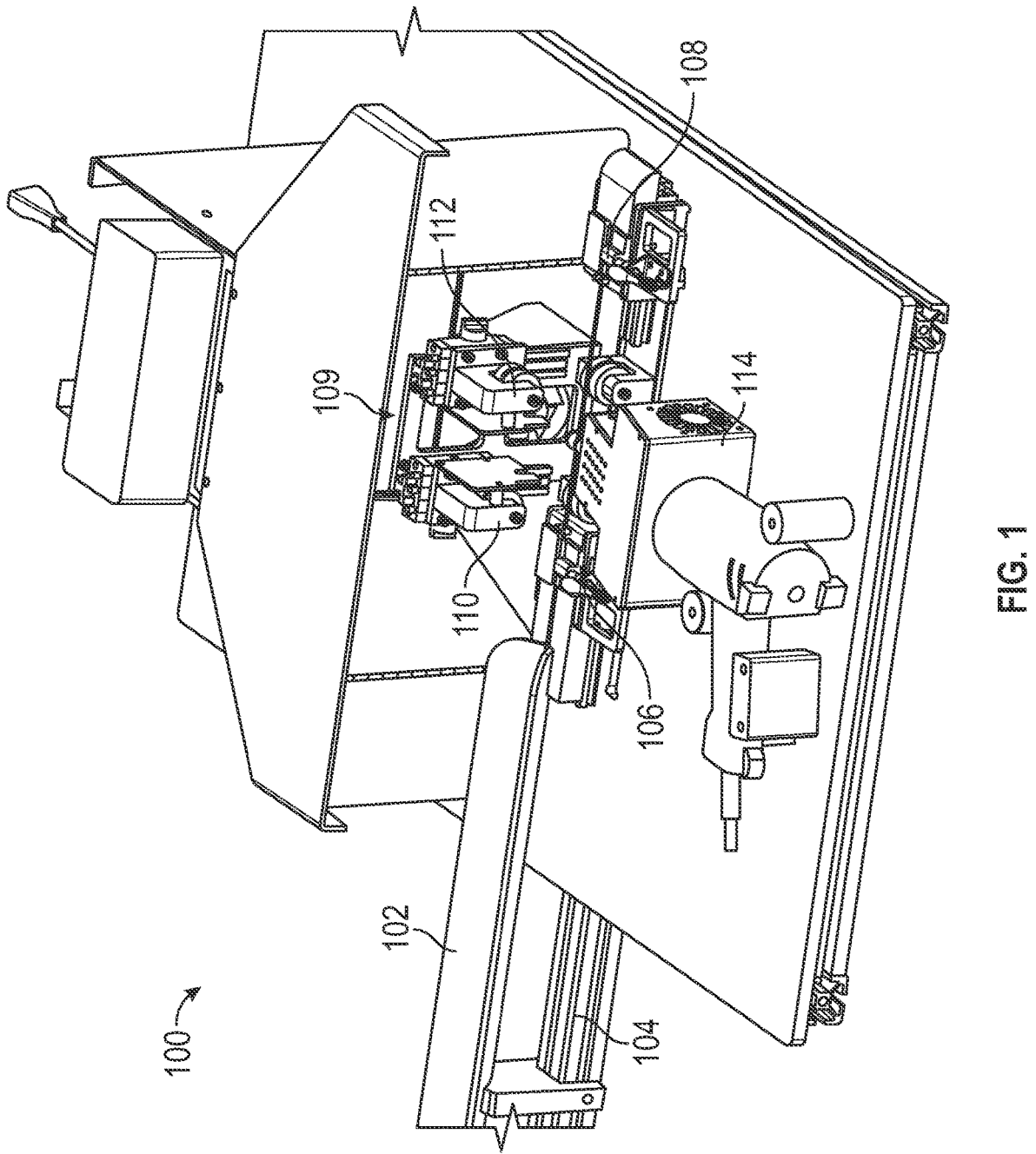
FIG. 1 illustrates a system for catheter reformation.

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout the above disclosure will now be presented.

The term "coupled" as used herein is defined as connected, whether directly or indirectly through intervening components, and is not necessarily limited to physical connections. The connection can be such that the objects are permanently connected or releasably connected.

The term "substantially" is defined to be essentially conforming to the particular dimension, shape or other word that substantially modifies, such that the component need not be exact.

The term "about" means reasonably close to the particular value. For example, about does not require the exact measurement specified and can be reasonably close. For example, the term "about" can include the number plus-or-minus 30%. In some examples, the word "about" can include the exact number.

The terms "comprising," "including" and "having" are used interchangeably in this disclosure. The terms "comprising," "including" and "having" mean to include, but not necessarily be limited to the things so described.

The present disclosure relates to a catheter restoration system and methods operable to remove kinks and/or reform a catheter of a medical device. The system is operable to remove kinks from catheters that were previously used in a patient or catheters that have manufacturing defects from the original manufacture of the device. Further, the system can reform catheters back to an as-manufactured condition and/or within medical grade tolerances for use in a patient. The system can include a heat device operable to soften the kinked or damaged material of the catheter and a reforming assembly operable to reform the kinked or damaged material to a uniform and consistent diameter.

FIG. 1 illustrates the catheter restoration system 100. The catheter restoration system 100 can be operable to reform a kinked or damaged surface of a catheter 232 of a medical device 702. The medical device 702 can be a medical device 702 with a catheter 232, as illustrated, for example in FIGS. 7-9. The medical device 702 can be any type of medical device 702 that includes a catheter 232. For example, the medical device 702 could be an imaging catheter (e.g., ultrasound imaging catheters). In some examples, the medical device 702 can have a body 704, as illustrated, for example, in FIGS. 7-9. In some examples, the medical device 702 can have a catheter 232, as illustrated, for example, in FIGS. 2, 3, 7, 8, and 9. The catheter restoration system 100 can be operable to heat an exterior surface of a catheter 232 via a heating device 114, as illustrated for example, in FIGS. 1, 2, 3, 7, and 11. The heat device 114 can be operable to provide heat to the catheter 232 such that the exterior surface of the catheter 232 softens. Softening the exterior surface of the catheter 232 can allow for the catheter to become moldable (e.g., the form or shape of the exterior surface of the catheter 232 can be changed). For example, the softened or moldable exterior surface can be formed into a desired shaped by applying a pressure or force to the exterior surface. The pressure or force can be applied by a reforming assembly 109 operable to shape or mold the softened material into a desired shape (e.g., a consistent diameter). The pressure or force can be provided by a pair of rolling wheels (e.g., first wheel assembly 110 and/or second wheel assembly 112), as illustrated, for example, in FIG. 1, 2, 3, 5 or by a reforming split mold 1213, as illustrated for example, in FIGS. 12A-12C.

Reforming the catheter 232 to a desired shape (e.g., a consistent diameter) can allow the catheter to be reused in a patient. In some examples, the catheter 232 has been used in a patient previously and has been damaged (e.g., kinked). Damaged catheters with non-uniform diameters are unsafe for patient use because damaged catheters can have protrusions or indents which can damage arteries of a patient. By reforming the catheter 232, protrusions or indents in the catheter 232 can be removed, thereby providing a catheter 232 with a consistent uniform surface that is safe for patient use. For example, the catheter 232 can be reformed to an originally manufactured and clinically safe condition.

The catheter restoration system 100 can include a medical device tray 102 operable to hold the body 704 of the medical device 702. The medical device tray 102 can provide a stable surface for holding the medical device 702, thereby preventing unwanted motion of the medical device 702 such as rolling, rotation, tipping, or other unwanted motion. The medical device tray 102 can also provide for precise control over the movement of the medical device 702 such as translating the medical device 702 throughout the system. In some examples, the medical device tray 102 can include a V-shaped tray such that the medical device tray 102 can hold the body 704 of the medical device 702 without the body 704 of the medical device 702 rolling or moving undesirably. In some examples, the medical device tray 102 can be U-shaped or have other shapes operable to hold the body 704 of the medical device 702. Accordingly, the medical device tray 102 can maintain the position of the medical device 702 and provide precision, accuracy, and consistency when maneuvering the medical device 702.

The medical device tray 102 can be slidably coupled to a device tray guide rail 104. The device tray guide rail 104 can allow for motion of the medical device tray 102. The medical device tray 102 can be operable to translate along the device tray guide rail 104. In some examples, the device tray guide rail 104 can be operable to cause the medical device tray 102 to translate, for example, along a longitudinal axis. The device tray guide rail 104 can be configured to allow the medical device tray 102 to slide back and forth along a single axis defined by the device tray guide rail 104. As the medical device tray 102 translates, the medical device 702 and/or the catheter 232 can be caused to translate as well. In some examples, as the catheter 232 translates, the medical device tray 102 translates to prevent pulling on the catheter 232 by the medical device 702.

Figure 2:
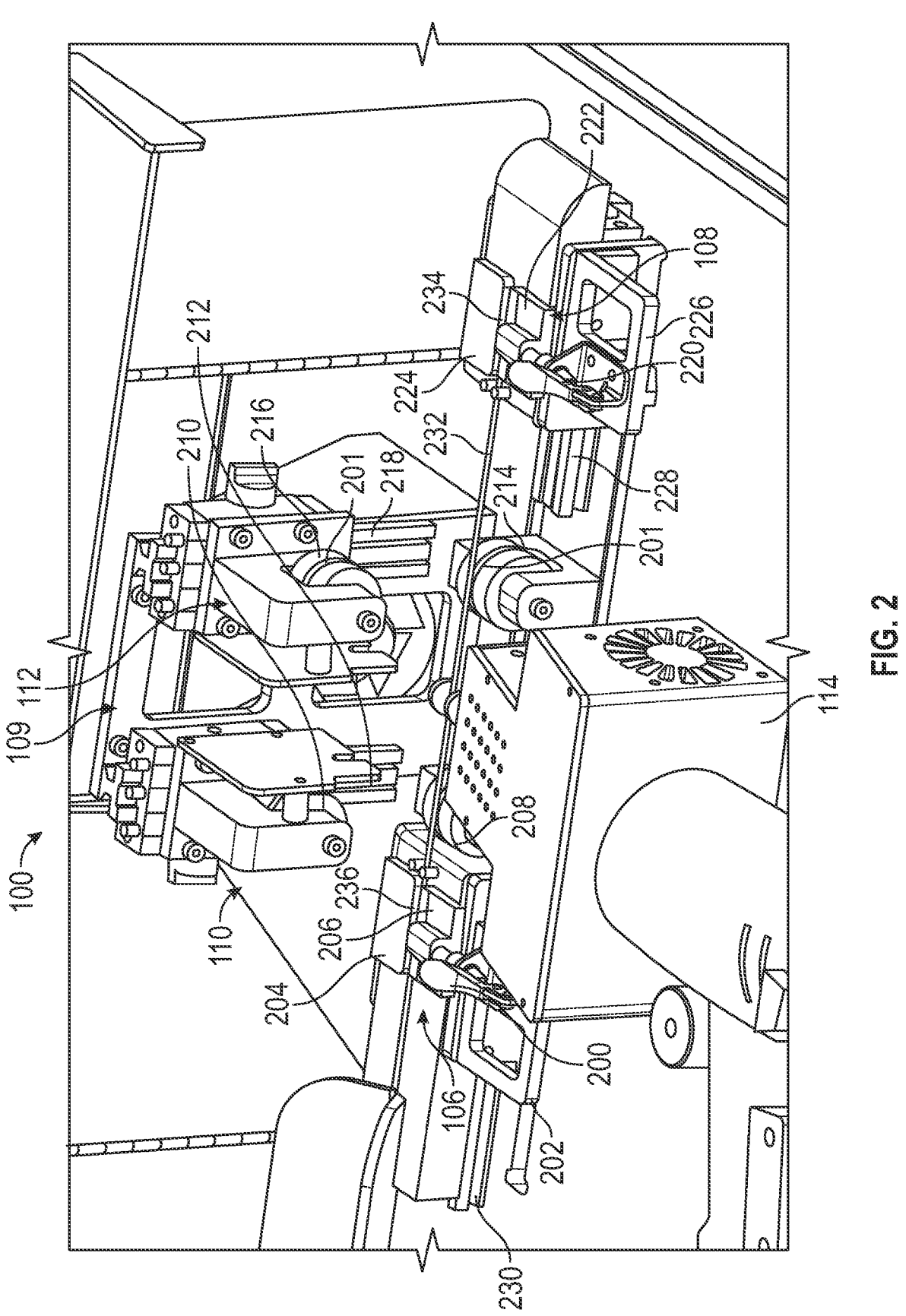
FIG. 2 illustrates the system for catheter reformation.
Figure 3:
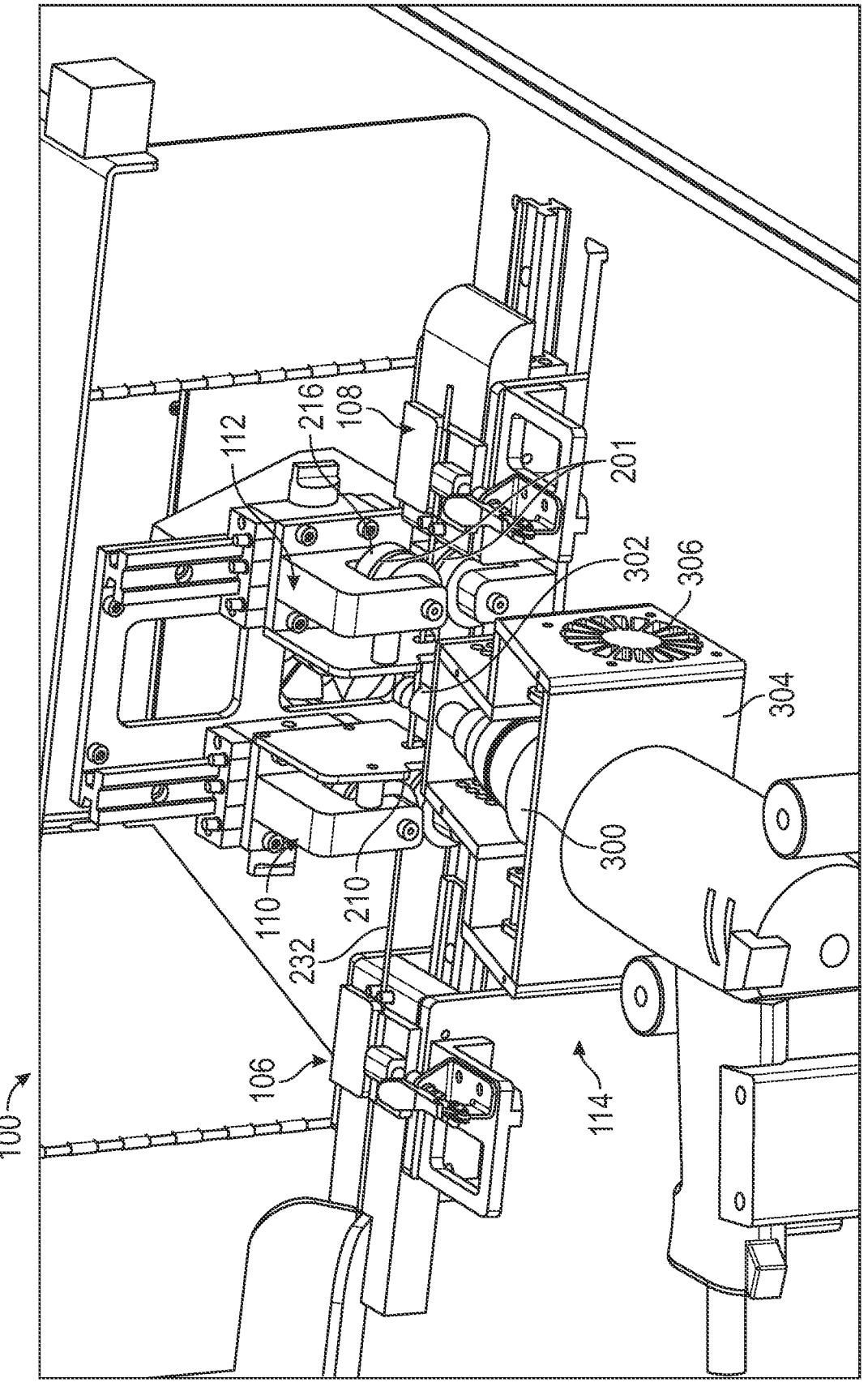
FIG. 3 illustrates the system for catheter reformation.

The catheter restoration system 100 can include a securing mechanism to secure the catheter 232. For example, the catheter restoration system 100 can include at least one clamp 106, 108 operable to secure the catheter 232. The at least one clamp 106, 108 can be operable to transition between an open configuration and a closed configuration. In the open configuration, the at least one clamp 106, 108 can be operable to receive the catheter (e.g., catheter 232 as shown in FIGS. 2-3). When in the closed configuration, the at least one clamp 106, 108 can be operable to compress against the catheter 232 to immobilize the catheter 232 in relation to the at least one clamp 106, 108. The at least one clamp 106, 108 can include any suitable type of clamping or securing mechanism operable to secure the catheter 232.

The at least one clamp 106, 108 can be operable to both secure the catheter 232 and move the catheter 232 throughout the catheter restoration system 100. For example, the at least one clamp 106, 108 can maneuver the catheter 232 through a reforming assembly 109. In at least one example, the reforming assembly 109 can include a first wheel assembly 110, a second wheel assembly 112, and/or a reforming split mold 1213. The reforming assembly 109 can be operable to reform the shape of the catheter 232 when the catheter 232 is translated along the longitudinal axis through the reforming assembly 109. In some examples, the at least one clamp 106, 108 can entirely control the motion of the catheter 232 once the catheter 232 is secured to the at least one clamp 106, 108. The at least one clamp 106, 108 can provide motion back and forth through the reforming assembly 109) by pushing and pulling the catheter 232 back and forth. The motion provided by the at least one clamp 106, 108 to the catheter 232 can allow a softened material (e.g., material heated by the heat device 114) of the catheter 232 to be moved back and forth through the reforming assembly 109. By moving the catheter 232 back and forth through the reforming assembly 109, any kinks or damage to the catheter 232 can be removed, thereby forming a uniform and consistent diameter of the catheter 232 and allowing the catheter 232 to be operable to be used in a patient safely.

In some examples, the at least one clamp 106, 108 can include a first clamp assembly 106 and a second clamp assembly 108. The first clamp assembly 106 and the second clamp assembly 108 can be operable to capture and hold a catheter 232 of the medical device 702 (for example as shown in FIGS. 2 and 3). The first clamp assembly 106 can be operable to secure the catheter 232 at a first location and the second clamp assembly 108 can be operable to secure the catheter 232 at a second location. The heat device 114 can be between the first clamp assembly 106 and the second clamp assembly 108 such that the catheter 232 is secured at two locations on opposing sides of the heat device 114. Similarly, the first clamp assembly 106 and the second clamp assembly 108 can secure the catheter 232 on opposite sides of the reforming assembly 109 such that the pulling the second clamp assembly 108 pulls the catheter 232 in a first direction through the reforming assembly 109 and pulling the first clamp assembly 106 pulls the catheter 232 in a second direction, opposite the first direction, through the reforming assembly 109. Similarly, pushing the first clamp assembly 106 moves the catheter 232 in the second direction, while pushing the second clamp assembly 108 moves the catheter 232 in the first direction. The first clamp assembly 106 and the second clamp assembly 108 can provide motion to the catheter 232 back and forth along a longitudinal axis in relation to the reforming assembly 109.

In some examples, the first clamp assembly 106 can be positioned proximal to the medical device tray 102. The first clamp assembly 106 can be positioned between the medical device tray 102 and the heat device 114. The second clamp assembly 108 can be positioned distal to the medical device tray 102. The second clamp assembly 108 can be positioned on an opposite side of the heat device 114 than the first clamp assembly 106 (e.g., the heat device 114 is between the first clamp assembly 106 and the second clamp assembly 108). The first clamp assembly 106 can be positioned between the second clamp assembly 108 and the medical device tray 102. The first clamp assembly 106 and the second clamp assembly 108 can be any suitable type of clamping or securing mechanism operable to secure the catheter 232 of the medical device 702.

The first clamp assembly 106 and/or the second clamp assembly 108 can be operable to transition between an open configuration and a closed configuration. In the open configuration, the first clamp assembly 106 and/or the second clamp assembly 108 can be operable to receive the catheter 232. When in the closed configuration, the first clamp assembly 106 and/or the second clamp assembly 108 can be operable to compress against the catheter 232 to immobilize the catheter 232 in relation to the first clamp assembly 106 and/or the second clamp assembly 108.

The catheter restoration system 100 can further include a reforming assembly 109. The reforming assembly 109 can be operable to reform an exterior surface of the catheter 232. In some examples, the reforming assembly 109 can be operable to reform the exterior surface of the catheter 232 to a consistent and uniform diameter such that the catheter 232 can have the same dimensions as an originally manufactured catheter, thereby allowing the catheter 232 to be used in a patient after a previous use. For example, the reforming assembly 109 can have a reforming component 201 operable to form the exterior surface of the catheter 232 into a uniform diameter. For example, the reforming component 201 can receive a kinked or damaged portion of the catheter 232 therein and provide a pressure or force to the catheter 232, thereby smoothing any protrusions and moving the material from the protrusion to an indent in the exterior surface of the catheter 232 when the catheter is moved along a longitudinal axis through the reforming assembly 109. In some examples, the reforming component 201 can be a hole, a series of holes, a groove, a channel or other geometries having a diameter equal to a desired diameter of the catheter 232. In some examples, the kinked or damaged portion of the exterior surface of the catheter 232 is heated, thereby softening the exterior surface and allowing the exterior surface to be moldable, before the catheter 232 is reformed by the reforming assembly 109. In some examples, the at least one clamp 106, 108 is operable to translate or move the catheter 232 through the reforming assembly 109. In some examples, the reforming assembly 109 is moveable along a length of the catheter 232.

The reforming assembly 109 can be located between the first clamp assembly 106 and the second clamp assembly 108. In some examples, the reforming assembly 109 can be located between the first clamp assembly 106 and the heat device 114. In some examples, the reforming assembly 109 can be located between the heat device 114 and the second clamp assembly 108. In some examples, multiple reforming assemblies 109 can be located between the first clamp assembly 106 and the second clamp assembly 108. For example, a first reforming assembly 109 can be located between the first clamp assembly 106 and the heat device 114 and a second reforming assembly 109 can be located between the heat device 114 and the second clamp assembly 108. In some examples, when the at least one clamp 106, 108 is a single clamp, the reforming assembly 109 can be located between the at least one clamp 106, 108 and the heat device 114. In some examples, when the at least one clamp 106, 108 is a single clamp, the heat device 114 can be between the reforming assembly 109 and the at least one clamp 106, 108.

In some examples, the reforming assembly 109 can include a first wheel assembly 110 and/or a second wheel assembly 112. The first wheel assembly 110 can be operable to reform the catheter 232 by receiving the catheter 232 between grooves (reforming component 201, for example, grooves 506, 508) in two rolling wheels 208, 210, thereby providing a pressure or force to the catheter 232 and forming a uniform diameter by smoothing any protrusions or indents in the catheter 232. The second wheel assembly 112 can be operable to reform the catheter between grooves (for example grooves 506, 508) in two rolling wheels 214, 216, thereby providing a pressure or force to the catheter 232 and forming a uniform diameter by smoothing any protrusions or indents in the catheter 232. In some examples, the reforming component 201 can be corresponding grooves (e.g., grooves 506, 508) in a circumference of each wheel 208, 210 of the pair of rolling wheels 208, 210.

In at least one example, the first wheel assembly 110 can be located between the first clamp assembly 106 and the second clamp assembly 108. In some examples, the first wheel assembly 110 can be located between the first clamp assembly 106 and the heat device 114. The second wheel assembly 112 can be located between the first clamp assembly 106 and the second clamp assembly 108. In some examples, the second wheel assembly 112 can be located between the heat device 114 and the second clamp assembly 108. In some examples, the first wheel assembly 110 can be located between the first clamp assembly 106 and the second wheel assembly 112. In some examples, the heat device 114 can be located between the first wheel assembly 110 and the second wheel assembly 112. In some examples, the catheter restoration system 100 can have a single wheel assembly or three or more wheel assemblies. In some examples, the single wheel assembly (e.g., first wheel assembly 110 or second wheel assembly 112) can be located between the heat device 114 and the first clamp assembly 106 or between the heat device 114 and the second clamp assembly 108.

As illustrated in FIG. 2, the first clamp assembly 106 can include a toggle component 200, a handle 202, a first clamping portion 206, and a second clamping portion 204. The toggle component 200 can be operable to transition between an unlocked position and a locked position. When the toggle component 200 is in the unlocked position, the first clamping portion 206 and/or the second clamping portion 204 can move relative to one another. When the toggle component 200 is in the locked position, the first clamping portion 206 and/or the second clamping portion 204 can be prevented from moving relative to one another. In at least one example, the toggle component 200 can include a clamp. In some examples, the toggle component 200 can include a button, an actuator, a motor, a braking system, etc. without deviating from the scope of the disclosure.

The first clamping portion 206 and the second clamping portion 204 can define a gap 236. The gap 236 can be operable to receive a portion of a catheter 232. In some examples, the first clamping portion 206 can be operable to move perpendicular to the longitudinal axis of the catheter 232 (e.g., axis defined by a length of the catheter 232) when the toggle component 200 is in an unlocked position. In some examples, the first clamping portion 206 can include a moveable clamping portion. In some examples, the second clamping portion 204 can be static (e.g., remain in a fixed position). The first clamping portion 206 can be pushed towards the catheter 232 such that it exerts a securing force on the catheter 232 against the second clamping portion 204. In some examples, the first clamping portion 206 and the second clamping portion 204 can both be moveable and can transition between open and closed configurations (e.g., increase and decrease the size of the gap 236). The toggle component 200 can then be actuated to a locked position, thereby locking the moveable clamping portion 206 in place and securing the catheter 232 in the first clamp assembly 106. In some examples, actuating the toggle component 200 to the locked position can automatically move the first clamping portion 206 and/or second clamping portion 204 towards the catheter 232, and actuating the toggle component 200 to the unlocked position can automatically move the first clamping portion 206 and/or second clamping portion 204 away from the catheter 232. It will be appreciated that other mechanisms can be used as alternatives to, or in conjunction with, the first clamp assembly 106 to secure the catheter 232 in relation to the medical device tray 102.

As illustrated in FIG. 2, the second clamp assembly 108 can include a toggle component 220, a handle 202, a first clamping portion 222, and a second clamping portion 224. The toggle component 220 can be operable to transition between an unlocked position and a locked position. When the toggle component 220 is in the unlocked position, the first clamping portion 222 and/or the second clamping portion 224 can move relative to one another. When the toggle component 220 is in the locked position, the first clamping portion 222 and/or the second clamping portion 224 can be prevented from moving relative to one another. In at least one example, the toggle component 220 can include a clamp. In some examples, the toggle component 220 can include a button, an actuator, a motor, a braking system, etc. without deviating from the scope of the disclosure.

The first clamping portion 222 and the second clamping portion 224 can define a gap 234. The gap 234 can be operable to receive a portion of a catheter 232. In some examples, the first clamping portion 222 can be operable to move perpendicular to the longitudinal axis of the catheter 232 (e.g., axis defined by a length of the catheter 232) when the toggle component 220 is in an unlocked position. In some examples, the first clamping portion 222 can be a moveable clamping portion. In some examples, the second clamping portion 224 can be static (e.g., remain in a fixed position). The first clamping portion 222 can be pushed towards the catheter 232 such that it exerts a securing force on the catheter 232 against the second clamping portion 224. In some examples, the first clamping portion 222 and the second clamping portion 224 can both be moveable and can transition between open and closed configurations (e.g., increase and decrease the size of the gap 234). The toggle component 220 can then be actuated to a locked position, thereby locking the moveable clamping portion 222 in place and securing the catheter 232 in the second clamp assembly 108. In some examples, actuating the toggle component 220 to the locked position can automatically move the first clamping portion 222 and/or second clamping portion 224 towards the catheter 232, and actuating the toggle component 220 to the unlocked position can automatically move the first clamping portion 222 and/or second clamping portion 224 away from the catheter 232. It will be appreciated that other mechanisms can be used as alternatives to, or in conjunction with, the second clamp assembly 108 to secure the catheter 232 in relation to the medical device tray 102.

In some examples, the catheter 232 is secured to the first clamping assembly 106 and the second clamping assembly 108 such that the damaged or kinked portion of the catheter 232 is between the first clamp assembly 106 and the second clamp assembly 108. In some examples, the first clamp assembly 106 and the second clamp assembly 108 provide tension to the catheter 232 between the first clamp assembly 106 and the second clamp assembly 108. For example, the catheter 232 can be secured to the first clamp assembly 106 first and then pulled tight before securing the catheter 232 to the second clamp assembly 108 such that there is tension in the catheter 232 between the first clamp assembly 106 and the second clamp assembly 108. In some examples, the catheter 232 can be secured to the second clamp assembly 108 first and then pulled tight before securing the catheter 232 to the first clamp assembly 106 such that there is tension in the catheter 232 between the first clamp assembly 106 and the second clamp assembly 108. In some examples, the tension in the catheter 232 between the first clamp assembly 106 and the second clamp assembly 108 can ensure that the catheter 232 remains in line with an axis defined by the reforming component 201 of the reforming assembly 109 such that the material of the exterior surface of the catheter 232 is smooth after moving through the reforming assembly 109.

In some examples, the at least one clamp 106, 108 is moveable (e.g., slidable) along a guide rail (e.g., first clamp assembly guide rail 230 and/or second clamp assembly guide rail 228). The at least one clamp 106, 108 can be moveable back and forth along an axis defined by the guide rail (e.g., first clamp assembly guide rail 230 and/or second clamp assembly guide rail 228). In some examples, the first clamp assembly 106 can be slidably coupled to a first clamp assembly guide rail 230. For example, the first clamp assembly 106 can be operable to move, slide, and translate along the first clamp assembly guide rail 230. The second clamp assembly 108 can be slidably coupled to a second clamp assembly guide rail 228. For example, the second clamp assembly 108 can be operable to move, slide, and translate along the second clamp assembly guide rail 228. In some examples, the first clamp assembly 106 and the second clamp assembly 108 can be slidably mounted to a single clamp guide rail (e.g., first clamp assembly guide rail 230 and/or second clamp assembly guide rail 228). In some examples, the first clamp assembly 106 and the second clamp assembly 108 can be slidably mounted to the device tray guide rail 104.

In some examples, the first clamp assembly 106 and the second clamp assembly 108 can be manually moved, slid, and/or translated along the first clamp assembly guide rail 230 and the second clamp assembly guide rail 228, respectively, by an operator. Once the catheter 232 has been secured by the first clamp assembly 106 and the second clamp assembly 108, the catheter 232 moves with the first clamp assembly 106 and the second clamp assembly 108 along the first clamp assembly guide rail 230 and the second clamp assembly guide rail 228. Similarly, the body 704 of the medical device 702 (e.g., the portion of the medical device 702 held in the medical device tray 102) can move with the medical device tray 102 along the device tray guide rail 104. In this manner, the medical device 702 is moveable along an axis defined by the guide rails 104, 228, 230 within the catheter restoration system 100. In some examples, handles 202, 226 can allow an operator to slide the first clamp assembly 106 and the second clamp assembly 108 along the first clamp assembly guide rail 230 and the second clamp assembly guide rail 228. In some examples, the first clamp assembly 106 and the second clamp assembly 108 can be caused to be moved, translated, or slid by a motor or an actuator in communication with a controller (for example controller 1300 as illustrated in FIG. 13). In some examples, the at least one clamp 106, 108 can be caused to move by other movement mechanisms (e.g., either automated or manual movement mechanisms).

While three separate guide rails are depicted (e.g., medical device guide rail 104, first clamp assembly guide rail 230, and second clamp assembly guide rail 228), it will be appreciated that the catheter restoration system 100 can have a single guide rail configured to allow slidable mounting of the medical device tray 102, first clamp assembly 106, and second clamp assembly 108. In some examples, the catheter restoration system 100 can include two guide rails-a device tray guide rail 104 and a guide rail for slidably coupling the first clamp assembly 106 and the second clamp assembly 108. In some examples, when the at least once clamp 106, 108 is a single clamp, the single clamp can be slidably coupled to a guide rail (e.g., device tray guide rail 104, first clamp assembly guide rail 230, or second clamp assembly guide rail 228).

The catheter restoration system 100 can include at least one wheel assembly 110, 112 (reforming assembly 109) operable to provide a pressure or a surface to an exterior surface of the catheter 232. The pressure or force can be operable to smooth out (e.g., form a uniform or consistent diameter by removing protrusions and filling indents) a damaged or kinked portion of the catheter 232. As illustrated in FIG. 2, the catheter restoration system 100 can include a first wheel assembly 110 and a second wheel assembly 112. The first wheel assembly 110 can include a pair of rolling wheels (e.g., a lower wheel 208 and an upper wheel 210). The rolling wheels (e.g., lower wheel 208 and upper wheel 210) can be operable help guide the motion of the catheter 232 through the wheels (e.g., lower wheel 208 and upper wheel 210). For example, as the rolling wheels (e.g., lower wheel 208 and upper wheel 210) receive the catheter 232, the rolling wheels (e.g., lower wheel 208 and upper wheel 210) can rotate in a direction corresponding to the motion of the catheter 232, thereby allowing ease of motion by the catheter 232 between the rolling wheels (e.g., lower wheel 208 and upper wheel 210). The rolling wheels (e.g., lower wheel 208 and upper wheel 210) can ensure that the catheter 232 remains in the grooves (406, 506, 508) by guiding the motion of the catheter 232 (e.g., the rotation of the wheels 208, 210 guides the catheter 232 to remain within the grooves 406, 506, 508).

Figures 4, 5:
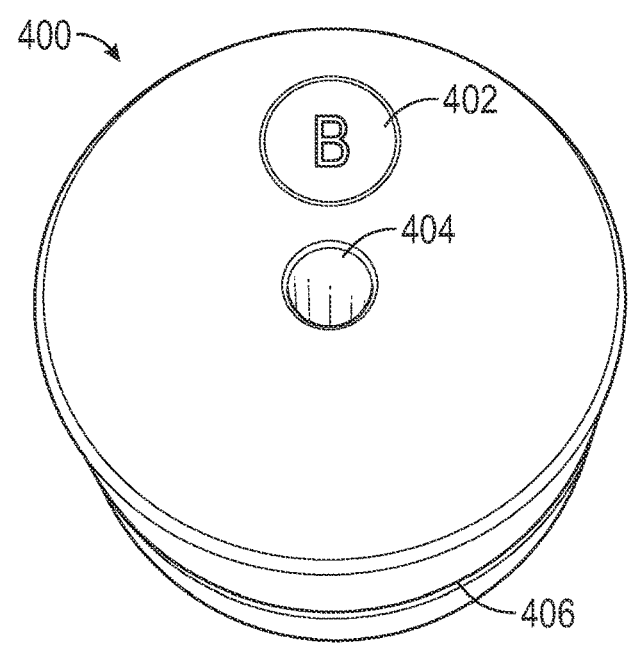
FIG. 4 illustrates a wheel.
FIG. 5 illustrates a wheel assembly.

The first wheel assembly 110 can be located between the first clamp assembly 106 and the second clamp assembly 108. In some examples, the first wheel assembly 110 can be located between the first clamp assembly 106 and the heat device 114. In some examples, the lower wheel 208 can be fixed in position such that the lower wheel 208 cannot translate in any direction but can rotate. The upper wheel 210 can be coupled to a rod 512 within a housing 518 (as shown in FIG. 5). The housing 518 can be moveable along a first wheel assembly guide rail 212, thereby allowing the vertical position of the upper wheel 210 to be adjustable. For example, the upper wheel 210 can be in a raised position (e.g., not contacting the lower wheel 208) while the catheter 232 is being secured in the at least one clamp (e.g., first clamp assembly 106 and the second clamp assembly 108). Once the catheter 232 is secured, the upper wheel 210 can be lowered such that the upper wheel 210 contacts the catheter 232 by moving the housing 518 and rod 510 connected to the upper wheel 210 downward along the first wheel assembly guide rail 212.

The second wheel assembly 112 can have a pair of rolling wheels (e.g., lower wheel 214 and upper wheel 216). The second wheel assembly 112 can be located between the first clamp assembly 106 and the second clamp assembly 108. In some examples, the second wheel assembly 112 can be located between the heat device 114 and the second clamp assembly 108. In some examples, the lower wheel 214 can be fixed in position such that the lower wheel 214 cannot translate in any direction and can only rotate. The upper wheel 216 can be rotatably coupled to a rod 510 within a housing 518 (as shown, for example, in FIG. 5). The housing

518 can be moveable along a second wheel assembly guide rail 218, thereby allowing the vertical position of the upper wheel 216 to be adjustable. For example, the upper wheel 216 can be in a raised position while the catheter 232 is being secured in the at least one clamp (e.g., first clamp assembly 106 and the second clamp assembly 108). Once the catheter 232 is secured, the upper wheel 216 can be lowered toward the lower wheel 214 such that the upper wheel 216 contacts the catheter 232 by moving the housing 518 and rod 510 connected to the upper wheel 216 downward along the second wheel assembly guide rail 218.

In some examples, the upper wheels 210, 216 can be manually locked at a vertical position along the first wheel assembly guide rail 212 and the second wheel assembly guide rail 218 using a toggle component or other locking mechanisms suitable to secure the upper wheels 210, 216 at a desired vertical position within the catheter restoration system 100 without deviating from the present disclosure. In other examples, the height of the upper wheels 210, 216 can be adjusted by a controller 1300 using a motor or actuator, as described further herein.

FIG. 2 illustrates the catheter restoration system 100 in a loading position. The loading position allows the catheter 232 to be secured in the at least one clamp (e.g., first clamp assembly 106 and second clamp assembly 108). After the catheter 232 has been secured to the at least one clamp 106, 108, the upper wheels 210, 216 can be lowered such that the upper wheels 210, 216 contact the respective lower wheels 208, 214. When the upper wheels 210, 216 contact the respective lower wheels 208, 214, the catheter restoration system 100 can be in a reforming position, as illustrated in FIG. 3. In the reforming position, the heat device 114 can provide heat to the catheter 232 and then the catheter 232 can be translated back and forth through the reforming assembly 109 thereby providing a pressure or force to the catheter 232 and forming a uniform diameter on the exterior surface of the catheter 232.

As illustrated in FIG. 3, the heat device 114 can be located between the first wheel assembly 110 and the second wheel assembly 112. The heat device 114 can have a thermal element 300 and a nozzle 302. The heat device 114 can also include a housing 304 having one or more vents 306. The one or more vents 306 can be operable to dissipate heat generated by the thermal element 300 out of the housing 304. The thermal element 300 can heat air or other gasses to a temperature and the nozzle 302 can be operable to provide the heated air to the catheter 232.

In some examples, the thermal element 300 can be configured to heat the air or other gasses to a temperature sufficient to soften the exterior surface of the catheter 232. In some examples, the temperature of the heated air and/or the duration the heated air provided is sufficient to soften the exterior surface of the catheter 232 without melting the catheter 232. The nozzle 302 can provide the heated air to a damaged surface of the catheter 232. For example, the catheter 232 may have a kink or other surface damage such that it needs to be reformed in order to meet certain tolerances for reuse in a patient. The kinked or damaged portion of the catheter 232 can be aligned with the nozzle 302 such that the heated air or gas is provided directly to the kinked or damaged portion. For example, the catheter 232 can be secured by the first clamp assembly 106 and the second clamp assembly 108 such that the kinked or damaged portion aligns with the nozzle 302. Once the kinked or damaged portion of the catheter 232 is softened, the catheter 232 can be reformed by the reforming assemblies (e.g., first wheel assembly 110 and/or second wheel assembly 112 and/or reforming split mold 1213) described herein.

The thermal element 300 can be operable to heat air or other gasses to a temperature of about 50 degrees Celsius (C) to about 55 degrees C., about 55 degrees C. to about 60 degrees C., about 60 degrees C. to about 65 degrees C., about 65 degrees C. to about 70 degrees C., about 70 degrees C. to about 75 degrees C., about 75 degrees C. to about 80 degrees C., about 80 degrees C. to about 85 degrees C., about 85 degrees C. to about 90 degrees C., about 90 degrees C. to about 95 degrees C., about 95 degrees C. to about 100 degrees C., about 100 degrees C. to about 105 degrees C., about 105 degrees C. to about 110 degrees C., about 110 degrees C. to about 115 degrees C., about 115 degrees C. to about 120 degrees C., about 120 degrees C. to about 125 degrees C., about 125 degrees C. to about 130 degrees C., about 130 degrees C. to about 135 degrees C., about 135 degrees C. to about 140 degrees C., about 140 degrees C. to about 145 degrees C., about 145 degrees C. to about 150 degrees C., about 150 degrees C. to about 155 degrees C., about 155 degrees C. to about 160 degrees C., about 160 degrees C. to about 165 degrees C., about 165 degrees C. to about 170 degrees C., or any range therebetween.

FIG. 4 illustrates an example of a wheel 400 (e.g., upper wheels 210, 216 and lower wheels 208, 214). The wheel 400 can include a marking 402, a hole 404, and a groove 406. The marking 402 can be indicative of the type of wheel. For example, the marking 402 can indicate the size of the groove 406. The groove 406 can extend along a circumference of the wheel 400. The groove 406 can be formed along the perimeter of the wheel 400. For example, the groove 406 can be formed in the lateral, external side of the perimeter of the wheel 400. The groove 406 can be operable to receive a portion of a diameter of the catheter 232 and a corresponding groove in another wheel can be operable to receive the remaining portion of the diameter of the catheter 232, for example as illustrated in FIG. 5. When the catheter 232 is received in the groove 406 and corresponding groove (e.g., grooves 506, 508 in FIG. 5), the grooves 506, 508 can provide a pressure or force to the catheter 232, thereby smoothing out the exterior surface of the catheter 232, removing any protrusions and filling any indents, and forming a uniform and consistent diameter on the exterior surface of the catheter 232. Different types of catheters can have different diameters. These different diameters can require different sized grooves in order to properly reform the catheter 232. For example, the grooves 406, 506, 508 can be operable to entirely enclose a diameter of the catheter 232 in order to reform the catheter 232, therefore, different sized catheters require different sized grooves 406, 506, 508. The marking 402 can be indicative of a wheel 400 to be used with catheters 232 having a certain diameter. The hole 404 can be operable to receive a rod 510 of the wheel assembly (e.g., first wheel assembly 110 and/or second wheel assembly 112), thereby allowing the wheels 400 to be interchangeable within the catheter restoration system 100. In this manner, different wheels 400 with different groove sizes can be selected for use in the catheter restoration system 100 depending on the type of catheter 232 to be reformed.

FIG. 5 illustrates an example of a wheel assembly 500 (e.g., first wheel assembly 110 and second wheel assembly 112). The wheel assembly 500 can be operable to reform the exterior surface of the catheter 232 to a uniform and consistent diameter. For example, the wheel assembly 110, 112, 500 can receive the catheter 232 between an upper wheel 210, 216, 502 and lower wheel 208, 214, 504 and provide a pressure or force to the catheter 232, thereby removing any protrusions and filling any indents in the catheter 232. The wheel assembly 500 can include an upper wheel housing 518, an upper wheel rod 512, an upper wheel rod head 514, an upper wheel 502, a lower wheel housing 520, a lower wheel rod 510, a lower wheel rod head 516, and a lower wheel 504.

The upper wheel 502 can be placed within the upper wheel housing 518 and the upper wheel rod 512 can be inserted through a hole in a proximal end of the upper wheel housing 518, a hole in the upper wheel 502, and a hole at the distal end of the upper wheel housing 518. The upper wheel rod head 514 can be pushed up against a surface of the upper wheel housing 518, thereby locking the upper wheel 502 in place within the upper wheel housing 518. The upper wheel 502 can rotate about the upper wheel rod 512. Similarly, the lower wheel 504 can be placed within the lower wheel housing 520 and the lower wheel rod 510 can be inserted through a hole in a proximal end of the lower wheel housing 520, a hole in the lower wheel 504, and a hole at the distal end of the lower wheel housing 520. The lower wheel rod head 516 can be pushed up against a surface of the lower wheel housing 520, thereby locking the lower wheel 504 in place within the lower wheel housing 520. The lower wheel 504 can rotate about the lower wheel rod 510.

In some examples, the upper wheel rod 512 and the lower wheel rod 510 can have threads on a side of the wheel rods 510, 512 opposite the wheel rod heads 514, 516. The upper wheel rod head 514 and the lower wheel rod head 516 can have slots for inserting a tool (e.g., screwdriver, Allen wrench, etc.). The upper wheel rod head 514 and the lower wheel rod head 516 can be rotated by the tool, thereby rotating the threads of the upper wheel rod 512 and the lower wheel rod 510 into corresponding threads in the holes on the distal side of the upper wheel housing 518 and the lower wheel housing 520 (e.g., side opposite of the insertion side of the wheel rods 510, 512). By rotating the threads of the upper wheel rod 512 and lower wheel rod 510 into corresponding threads of the upper wheel housing 518 and lower wheel housing 520, the upper wheel 502 and the lower wheel 504 are secured in the upper wheel housing 518 and the lower wheel housing 520. In some examples, the rods 510, 512 can have a snap fit mechanism to couple to the housings 518, 520. In some examples, the rods 510, 512 can have other mechanisms to couple to the housings 518, 520.

The upper wheel 502 can form a groove 506 and the lower wheel 504 can form a groove 508. As described herein, different wheels with different groove sizes can be used in the catheter restoration system 100 depending on the diameter of the catheter 232 to be restored. The groove 506 of the upper wheel 502 and the groove 508 of the lower wheel 504 are positioned such that the catheter 232 can be received within the grooves 506, 508. The grooves 506, 508 can then maintain the position of the catheter 232 while the catheter 232 is being translated back and forth through the upper wheel 502 and lower wheel 504. Both the groove 506 of the upper wheel 502 and the groove 508 of the lower wheel 504 are configured to contact the surface of the catheter 232 to reform the catheter 232. The grooves 506, 508 of the upper wheel 502 and lower wheel 504 can have substantially the same size and/or shape when used in the catheter restoration system 100. In other words, the upper wheel 502 and the lower wheel 504 can have the same groove size for a given catheter. In some examples, the upper wheel housing 518 and the lower wheel housing 520 are u-shaped wheel housings. Other wheel housing shapes can be used.

When the catheter 232 is heated by the heat device 114 and the exterior surface of the catheter 232 is softened, the catheter 232 can move or be translated along the at least one guide rail (e.g., device tray guide rail 104, first clamp assembly guide rail 230, and/or second clamp assembly guide rail 228). The catheter 232 can be reformed by contact of the catheter 232 with the grooves 506, 508 in the upper wheel 502 and lower wheel 504, thereby removing any kinks or damage to the exterior surface of the catheter 232. In some examples, the grooves 506, 508 are configured to enclose the diameter of the catheter 232. When the catheter 232 is translated through the grooves 506, 508, the grooves 506, 508 can smooth out any protrusions and move the extra material from the protrusions to corresponding indents, thereby forming a uniform and consistent diameter of the catheter 232. When the catheter 232 has a consistent and uniform diameter, the catheter 232 can have the same diameter as an originally manufactured catheter and be safe for clinical use in a patient. In some examples, when the catheter 232 is heated by the heat device 114 and the exterior surface of the catheter 232 is softened, the catheter 232 can be moved (e.g., by an operator) along the at least one guide rail (e.g., device tray guide rail 104, first clamp assembly guide rail 230, and/or second clamp assembly guide rail 228), thereby moving the catheter 232 back and forth through the grooves 506, 508. In some examples, when the catheter 232 is heated by the heat device 114 and the exterior surface of the catheter 232 is softened, the catheter 232 can be moved by a motor and/or actuator controlled by controller 1300 along the at least one guide rail (e.g., device tray guide rail 104, first clamp assembly guide rail 230, and/or second clamp assembly guide rail 228) thereby moving the catheter 232 back and forth through the grooves 506, 508.

Figure 6:
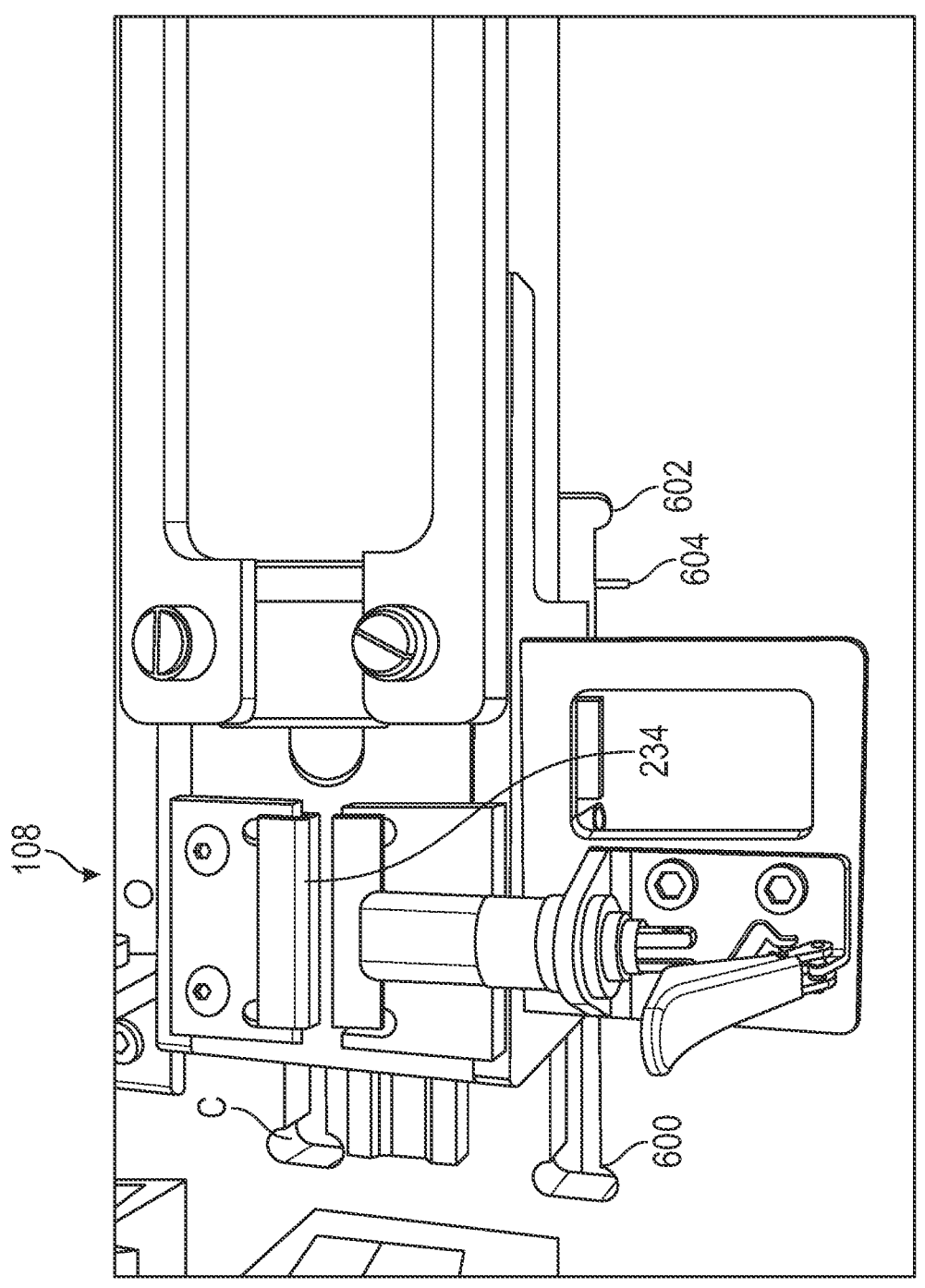
FIG. 6 illustrates a clamp assembly.

FIG. 6 illustrates the second clamp assembly 108. The second clamp assembly 108 can include a first end stop 600 and a second end stop 602. The first end stop 600 and the second end stop 602 can be operable to limit the distance the second clamp assembly 108, and thereby the first clamp assembly 106 and medical device tray 102, can move along the at least one guide rail (e.g., device tray guide rail 104, first clamp assembly guide rail 230, and/or second clamp assembly guide rail 228). In this manner, the first end stop 600 and the second end stop 602 can prevent movement of the second clamp assembly 108 beyond the end stops. Limiting the distance of movement can improve the efficiency of the catheter restoration system 100 by ensuring that the kinked or damaged portion of the catheter 232 is reformed by the wheel assembly 110, 112, 500 or wheel assemblies 110, 112, 500 without wasting additional time rolling unkinked or undamaged portions of the catheter through the wheel assembly 110, 112, 500 or wheel assemblies 110, 112, 500. While the first end stop 600 and second end stop 602 are shown for the second clamp assembly 108, it will be appreciated that the end stops could prevent movement of the first clamp assembly 106 or the medical device tray 102, since the first clamp assembly 106, second clamp assembly 108, and medical device tray 102 all move together when a catheter 232 is secured to the catheter restoration system 100.

In some examples, the second clamp assembly 108 can include a marker 604. The marker 604 can provide a measure for a distance to move the second clamp assembly 108, and thereby the first clamp assembly 106 and the medical device tray 102, along the guide rails (e.g., device tray guide rail 104, first clamp assembly guide rail 230, and/or second clamp assembly guide rail 228) to ensure sufficient contact of the kinked or damaged portion of the catheter 232 with the wheels 208, 210, 214, 216 of the wheel assemblies 110, 112. For example, the marker 604 can indicate to an operator to move the second clamp assembly 108 to the left of the marker 604, before moving the second clamp assembly 108 back to the second end stop 602.

Figure 7:
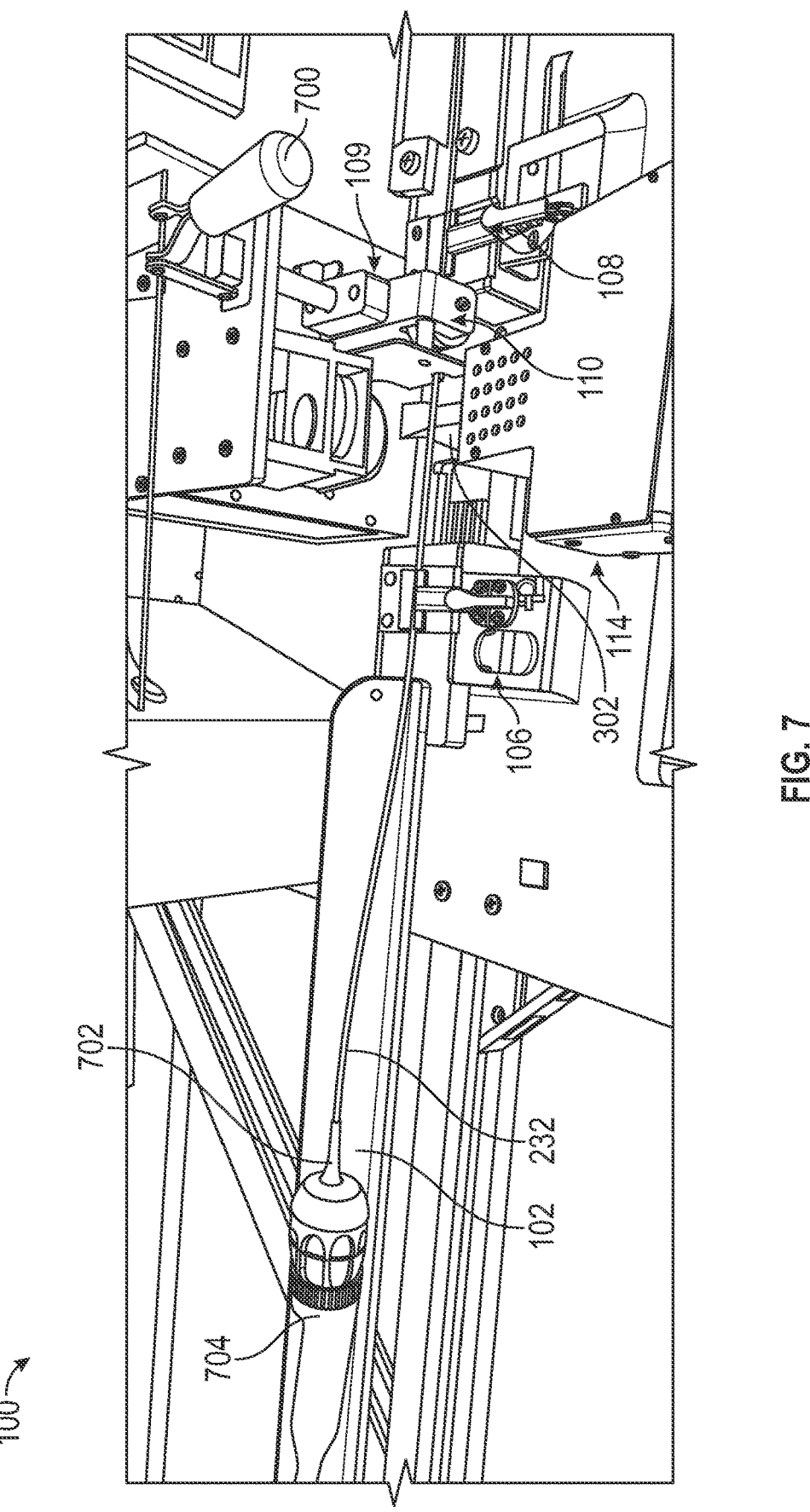
FIG. 7 illustrates a catheter reformation system.

FIG. 7 illustrates another example of a catheter restoration system 100. In the example as illustrated in FIG. 7, the catheter reformation system 100 can have a single reforming assembly 109 (e.g., first wheel assembly 110). The upper wheel 210 of the first wheel assembly 110 can have an adjustable vertical position within the catheter restoration system 100. The upper wheel toggle component 700 can lock the upper wheel 210 at a set vertical position. For example, when the catheter 232 is being loaded into the catheter restoration system 100, the upper wheel 210 can be locked at a maximum height (e.g., for ease of clamping the catheter 232 to the at least one clamp 106, 108). When the catheter 232 is loaded into the catheter restoration system 100 and the reformation process is ready to begin, the upper wheel toggle component 700 can be unlocked, the upper wheel 210 can be lowered such that the groove 506 of the upper wheel 210 contacts the surface of the catheter 232, and the upper wheel toggle component 700 can be locked, such that the grooves 506, 508 in the upper wheel 210 and lower wheel 208 are in contact with the catheter 232. In some examples, the toggle component 700 can be a manually actuated component (e.g., button, clamp, etc.) or an automated component (e.g., in communication with the controller 1300 and actuated by a motor, actuator, etc.)

FIG. 7 further illustrates the medical device 702 loaded in the catheter restoration system 100. The medical device 702 can include a body 704 which is held in the medical device tray 102 and a catheter 232 which is secured by the first clamp assembly 106 and the second clamp assembly 108. The kinked or damaged portion of the catheter 232 can be aligned with the nozzle 302 of the heat device 114. In this manner, the kinked or damaged portion of the catheter 232 can be provided heat first, and then once the kinked or damaged is softened, the kinked or damaged portion can be reformed by the grooves 506, 508 in the wheels 208, 210, 214, 216, 502, 504 in the wheel assembly 110, 112, 500. The grooves 506, 508 can enclose an entire diameter of the catheter 232 such that when the catheter is moved back and forth through the grooves 506, 508, the grooves 506, 508 move any excess material (e.g., material that extends outside of the desired diameter) to areas of the catheter 232 that have less material than desired (e.g., areas with indents that have insufficient amounts of material). In this manner, the catheter 232 can be smoothed out such that the catheter 232 has a uniform and consistent diameter.

Figure 8:
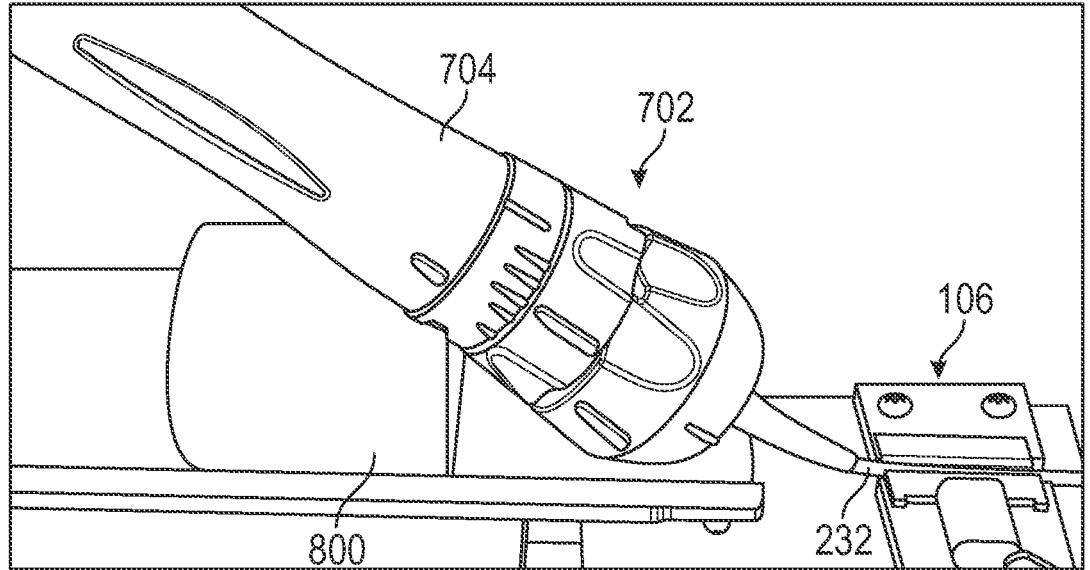
FIG. 8 illustrates a medical device body support.

FIG. 8 illustrates a body support 800 that can be operable to support the body 704 (e.g., handle) of the medical device 702. The body support 800 is configured to support the body 704 of the medical device 702 when the kink or damaged portion of the catheter 232 is close to the body 704. The body support 800 allows the catheter 232 near the body 704 to be closer to the plane of the first clamp assembly 106. In this manner, kinks and damaged portions near the body 704 can be reformed by the catheter restoration system 100.

Figure 9:
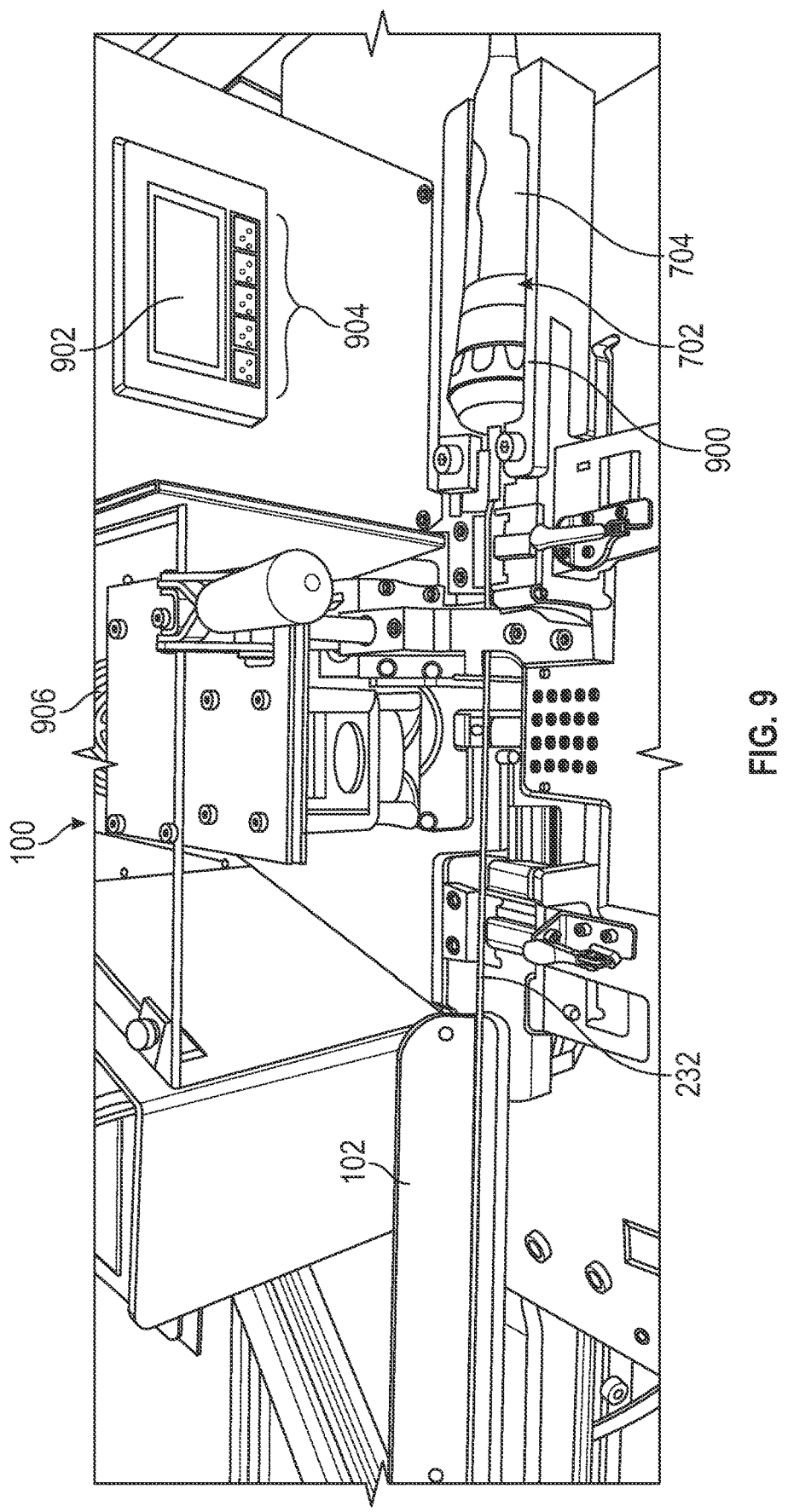
FIG. 9 illustrates a catheter reformation system.

FIG. 9 illustrates a catheter restoration system 100 loaded with a medical device 702. As illustrated in FIG. 9, the medical device 702 can be loaded in a reverse tray 900 opposite the medical device tray 102 (e.g., on the opposite side of the heat device 114). The reverse tray 900 can be located near the second clamp assembly 108 and on a side of the second clamp assembly 108 opposite the heat device 114. Accordingly, the reverse tray 900 is operable to receive the medical device 702 while the medical device tray 102 is operable to receive the catheter 232. The reverse tray 900 can provide another option for loading the medical device 702 to ensure the kinked or damaged portion of the catheter 232 is reformed. In some examples, the reverse tray 900 allows the catheter 232 to be installed in the catheter restoration system 100 along the same plane as the medical device 702, thereby preventing the catheter 232 from being bent in relation to the medical device 702.

In some examples, the catheter restoration system 100 can further include one or more fans 906, as illustrated in FIG. 9. The one or more fans 906 can be operable to provide cool air to the catheter 232 thereby shortening the cooling time of the catheter 232 after the catheter 232 has been reformed.

The catheter restoration system 100 can further include a display screen 902 and buttons 904. The display screen 902 can be in communication with a processor 1320 and/or controller 1300. The display screen 902 can be operable to display various instructions, statuses, and warnings regarding the operation of the catheter restoration system 100. For example, the display screen 902 can display instructions to choose a recipe (e.g., parameters such as temperature, heating duration, cooling duration, rolling duration, etc. for a type of catheter), secure the catheter 232 (e.g., connect device), ensure correct device positioning, begin heat device warmup, begin heating, begin rolling, cooling in progress, remove medical device, and confirm medical device restoration. The display screen 902 can further display a status of the catheter restoration system 100. For example, the display screen 902 can display a preheating status, a providing heat status, a ready for rolling status, a cooling status, or other statuses related to the operation of the catheter restoration system 100.

Figures 10A, 10B, 10C, 10D, 10E, 10F:
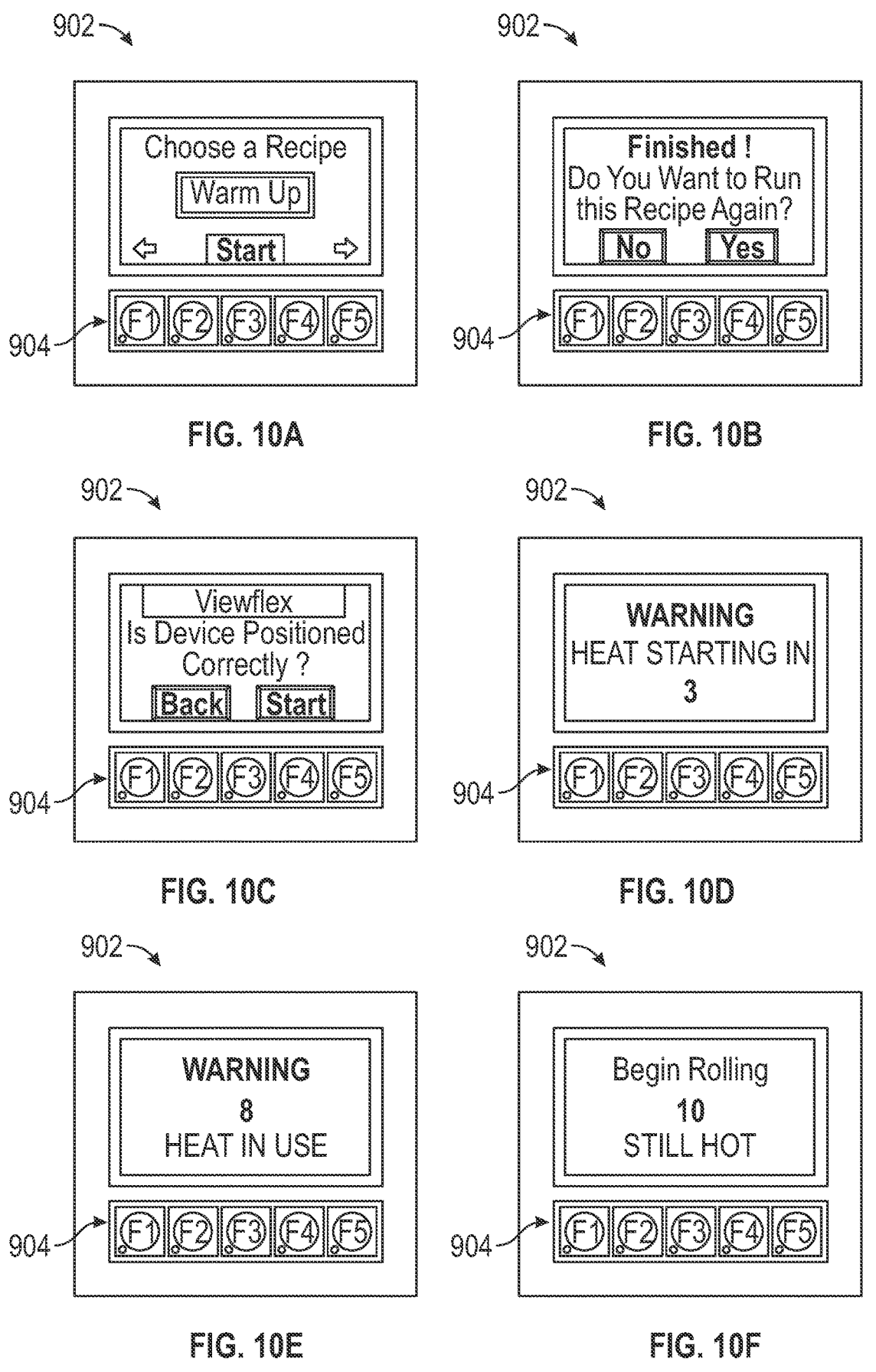

FIGS. 10A-10F illustrate examples of various instructions, statuses, and warnings that can be displayed on the display screen 902. As illustrated in FIG. 10A, the display screen 902 can display a choose recipe screen. The choose recipe screen can provide different recipes for different types of catheters. In some examples, the recipe can include the various parameters for a catheter 232 such as the wheel groove size to use, the temperature, the heated air duration, the roll time, the cooling time, and other parameters. As illustrated in FIG. 10B, the display screen 902 can display a run again screen, thereby allowing the operator to run the same recipe for another catheter of the same type or to rerun the system for the same catheter 232. As illustrated in FIG. 10C, the display screen 902 can display an instruction to have the operator ensure that the medical device 702 is properly positioned. As illustrated in FIG. 10D, the display screen 902 can display a warning that the heated air or gas from the heat device 114 is about to be provided to the catheter 232. In some examples, the warning can further include a countdown timer, thereby allowing the operator to know exactly when the heated air or gas will be applied to the catheter 232.

As illustrated in FIG. 10E, the display screen 902 can display a warning that heated air or gas is being provided to the catheter 232. In some examples, the warning can further include a countdown timer, thereby allowing the operator to know exactly when the heated air or gas will stop being provided to the catheter 232. As illustrated in FIG. 10F, the display screen 902 can display an instruction to begin rolling the softened material on the catheter 232. The begin rolling screen can be displayed after the catheter 232 has been heated such that the kinked or damaged portion of the catheter 232 has been softened. The begin rolling screen can further include a countdown timer, thereby informing the operator of how long to roll the catheter 232 (e.g., translate the catheter 232 back and forth along the at least one guide rail 104, 228, 230 between the wheel assembly 110, 112, 500 or wheel assemblies 110, 112, 500, thereby contacting the kinked or damaged portion of the catheter 232 with the grooves 506, 508 in the wheels 208, 210, 214, 216, 502, 504).

It will be appreciated that the display screen 902 can be operable to display any instructions, warnings, or statuses of the catheter restoration system 100. For example, the display screen 902 can display any instruction, warning, or status of the method described herein.

The buttons 904 can allow an operator to set and control various parameters of the catheter restoration system 100. For example, the buttons 904 can allow an operator to select parameters such as a temperature of heated air or gas provided by the heat device 114, a duration for the heated air or gas to be provided to the catheter 232, a fan speed, and a cooling duration. The buttons 904 can further allow the operator to electronically actuate the clamp assemblies 106, 108 and the wheel assemblies 110, 112 and translate the medical device 702 on the guide rails 104, 228, 230 when the clamp assemblies 106, 108 and wheel assemblies 110, 112 are electronically controllable (e.g., via motors and a processor 1320 and/or controller 1300 in communication with the motors).

In other examples, the display screen 902 can be a touch screen operable to receive inputs from an operator. In another example, the catheter restoration system 100 can have a controller 1300 and processor 1320 operable to be in wireless or wired communication with a computing device (e.g., mobile phone, computer, etc.). The computing device can control the operational parameters (e.g., temperature, duration of heating, clamp actuation, wheel height, motion of the medical device, etc.) of the catheter restoration system 100. In this manner, an operator can control the catheter restoration system 100 without having to manually actuate the various components. For example, motors can be used to drive the clamp assemblies 106, 108 along the guide rails 104, 228, 230, actuate clamp assemblies 106, 108 to secure the catheter 232, adjust the height of the upper wheel 210, 216 of the wheel assemblies 110, 112, and other various automated functions. Further, the processor 1320 and/or controller 1300 can be operable to cause the heat device 114 to warm up and provide heated air or gas to the catheter 232.

The catheter restoration system 100 can be connected to a power supply to power the heat device 114, the display screen 902, and any motors for actuating the various components of the catheter restoration system 100 as described herein.

Figure 11:
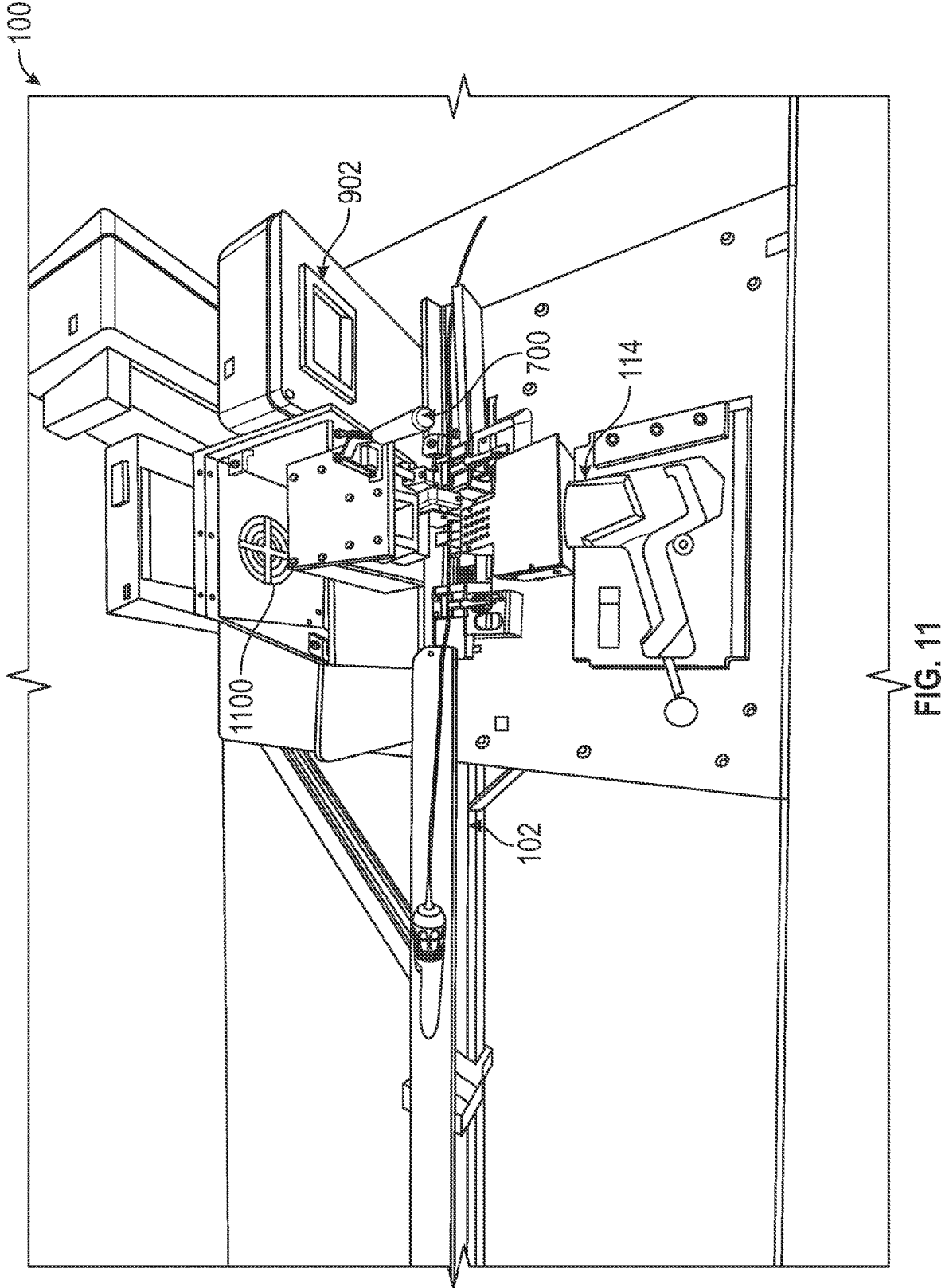
FIG. 11 illustrates another example of a catheter restoration system.

FIG. 11 illustrates the catheter restoration system 100. The catheter restoration system 100 can further include a fume fan 1100. For example, the fume fan 1100 can be configured to pull any fumes given off by the catheter 232 as it is provided the heated air or gas from the heat device 114. For example, once the heat device 114 begins providing heated air or gas to the catheter 232, the fume fan 1100 can be turned on and begin pulling any fumes given off by the catheter 232. The catheter restoration system 100 can further include a filter (e.g., fume scrubber) (not shown) operable to filter out the fumes. In some examples, the filter can be located within a housing that houses the fume fan 1100. The filter can be contained in the housing in the path of air pulled in by the fume fan 1110. The filter can be located behind the fume fan 1100, such that the fumes are pulled in by the fume fan 1100 and then filtered.

The fume fan 1100 can also act as a cooling fan after the softened material of the catheter 232 has been rolled. For example, after the catheter 232 has been rolled through the wheel assembly 110, 112, the fume fan 1100 can be configured to blow cool air towards the catheter 232 (i.e., the fume fan 1100 can operate in both a pulling air mode and a pushing air mode), thereby cooling the catheter 232. In some examples, the cooling fan can be its own component (e.g., the catheter restoration system 100 includes both a cooling fan 906 and a fume fan 1100).

The catheter restoration system 100 can be configured to reprocess any catheters that have kinks or damaged exterior surfaces. Non-limiting examples of catheters to be restored by the catheter restoration system include AcuNav, View-Flex, and SoundStar catheters. The wheel groove size can be chosen based on the type of catheter. For example, the groove size of the wheels 208, 210, 214, 216, 502, 504 can be configured to contact catheters having French sizes of 8, 9, 10 or other French sizes (e.g., diameters). Accordingly, the catheter restoration system 100 can accommodate and reprocess a variety of catheters, for example conventional catheters, imaging catheters, diagnostic catheters, treatment catheters, etc.

It will be appreciated that other configurations of the catheter restoration system 100 can be used. For example, as an alternative to, or in conjunction with, the slidable clamp assemblies 106, 108, the wheel assemblies 110, 112, 500 can be slidable along a length of the catheter 232. Further, the bottom wheel 208, 214 can have adjustable height while the upper wheel 210, 216 can have a fixed height.

Figure 12A:
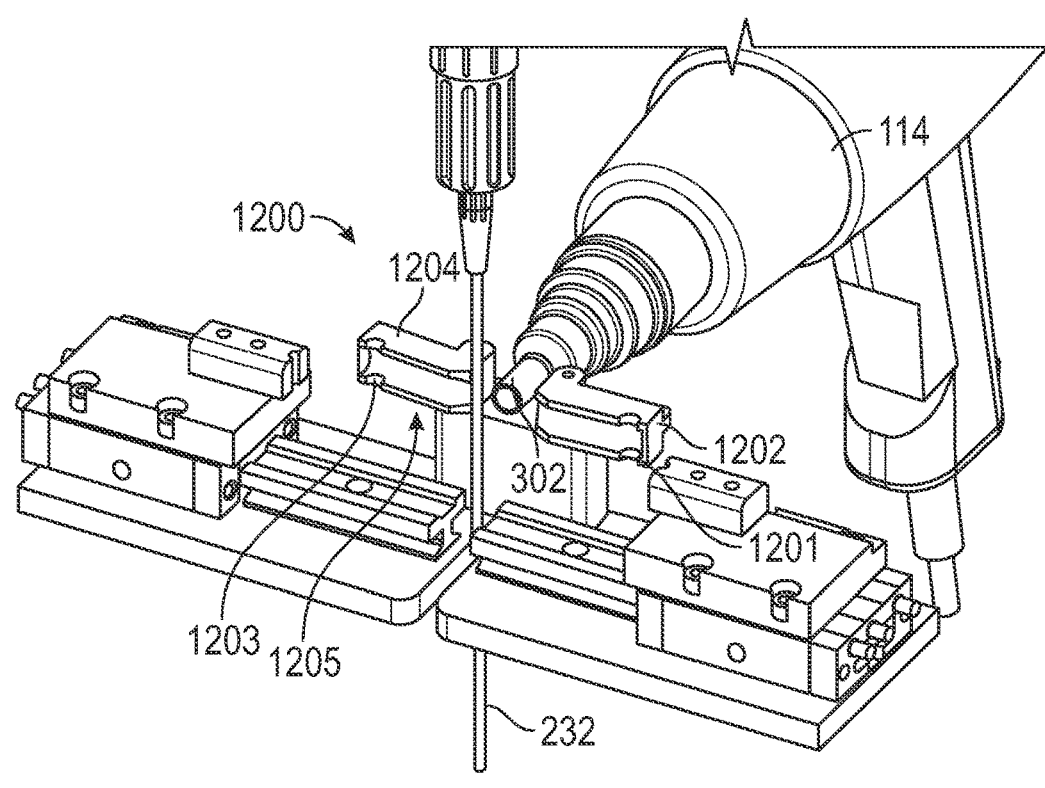
FIGS. 12A-12C illustrate an example of a split-mold reforming assembly.
Figure 12B:
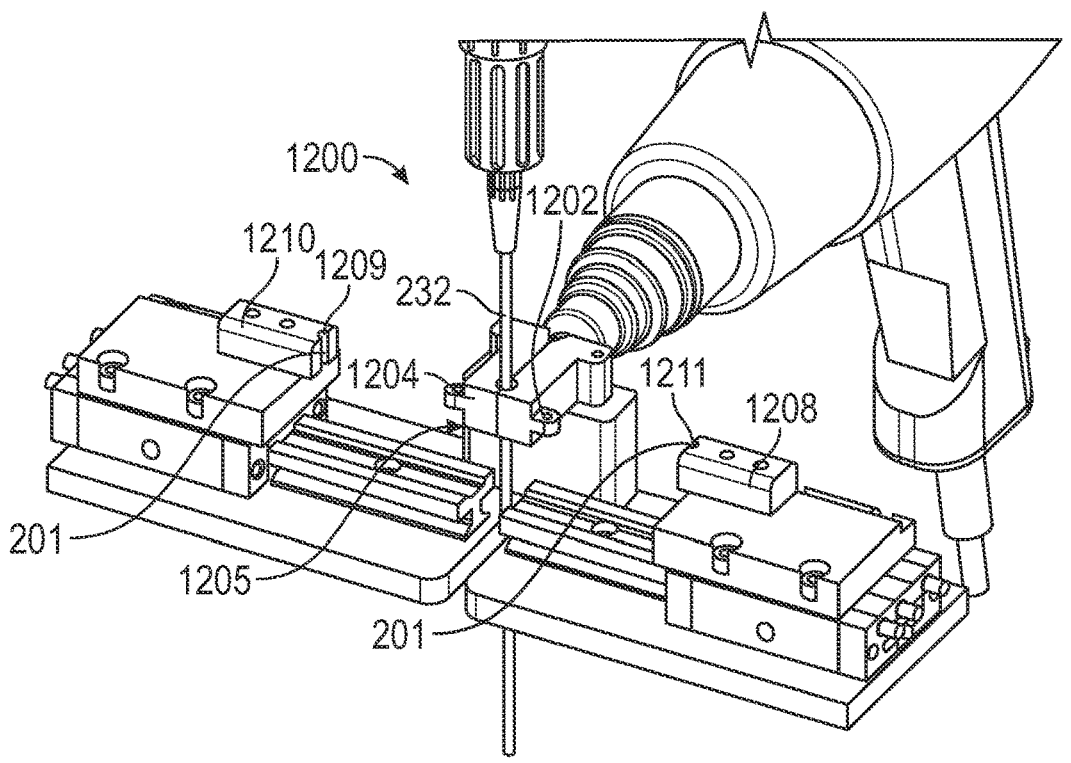
Figures 12C, 13:
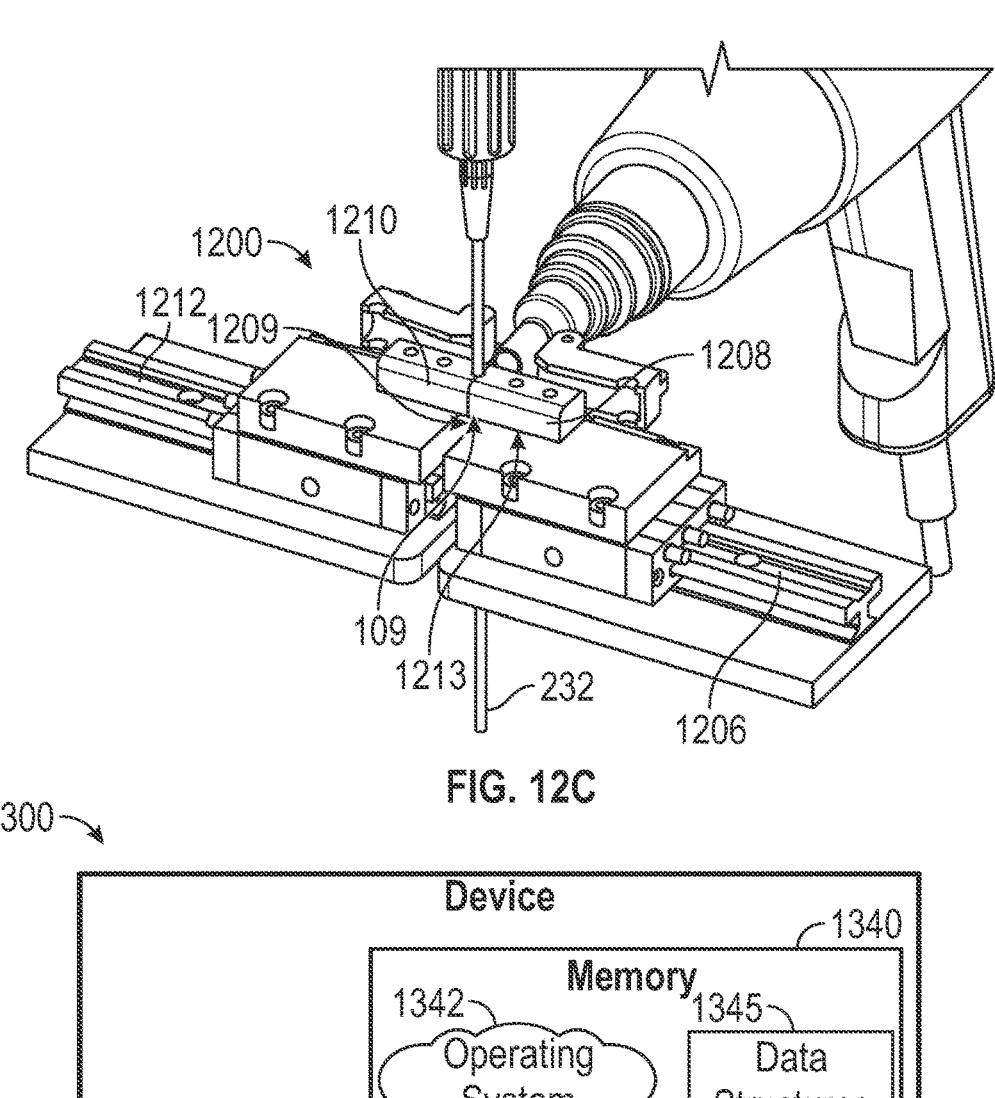
FIG. 13 is a schematic diagram of a controller.

FIGS. 12A-12C illustrates a split mold reforming assembly 1200. The split mold reforming assembly 1200 can have a heat split mold 1205 operable contain the kinked or damaged portion of the catheter 232 while heat is being applied to the kinked or damaged portion catheter 232 by the heat device 114. The split mold reforming assembly 1200 can include a reforming split mold 1213 (reforming assembly 109). The reforming split mold 1213 can be operable to enclose a diameter of the catheter 232 and reform the diameter of the catheter 232 to a desired diameter by translating the catheter 232 back and forth through the reforming component 201. In some examples, the reforming component 201 can be a hole formed by the connected reforming split mold 1213 (e.g., two half-circle holes 1209, 1211 forming a hole when the mold halves are connected). The hole (e.g., two half-circle holes 1209, 1211) can move excess material (e.g., protrusions) to areas of the catheter lacking material (e.g., indents), thereby smoothing out the diameter of the catheter 232 and reforming the catheter 232 to the catheter's 232 original diameter.

In some examples, the split mold reforming assembly 1200 can be used in conjunction with, or as an alternative to, the wheel assemblies 110, 112, 500 described herein. The split-mold reforming assembly 1200 can include a heat split mold 1205. The heat split mold 1205 can include a first heat mold half 1202 and a second heat mold half 1204. The kinked or damaged portion of the catheter 232 can be loaded into the heat split mold 1205. The first heat mold half 1202 and the second heat mold half 1204 can each form a half-circle hole 1201, 1203 to receive the damaged or kinked portion of the catheter 232, as illustrated in FIG. 12A. The first heat mold half 1202 and the second heat mold half 1204 can then be enclosed around the kinked or damaged portion of the catheter 232 (e.g., the kinked or damaged portion of the catheter 232 fits within the hole created by the two half-circle holes 1201, 1203). The first heat mold half 1202 and the second heat mold half 1204 can be operable to secure to one another via a locking mechanism (e.g., snap-fit mechanism, magnetic mechanism, etc.). Heated air or gas can then be applied to the kinked or damaged portion of the catheter 232 via the nozzle 302 of the heat device 114, as illustrated for example in FIGS. 12A-12B.

Once the catheter 232 has been heated such that the material is softened, the catheter 232 can be reformed by a reforming split mold 1213, as illustrated in FIG. 12C. The reforming split mold 1213 can include a first reforming half 1210 and a second reforming half 1208. The reforming split mold 1213 can have a reforming component 201. The first reforming half 1210 and the second reforming half 1208 can each have a half-circle hole 1209, 1211 which can combine to form a circle hole (reforming component 201). The half-circle holes 1209, 1211 can combine to form a circle hole (reforming component 201) having a diameter equal to the desired diameter of the catheter 232. When the first reforming half 1210 and the second reforming half 1208 are connected around the softened material, the catheter 232 can be translated back and forth through the circle hole (e.g., formed by the half-circle holes 1209, 1211), thereby reforming the kinked or damaged portion of the catheter 232 by removing protrusions and filling indents of the catheter 232. The catheter 232 then molds and reforms to the shape of the circle hole (e.g., formed by the two half-circle holes 1209, 1211) to fix the kinked and/or damaged portion of the catheter 232. The first reforming half 1210 and the second reforming half 1208 can each be connected to a guide rail 1212, 1206. The guide rails 1212, 1206 can be configured to allow movement of the first reforming half 1210 and second reforming half 1208 from an unconnected position to a connected position. The first reforming half 1210 and the second reforming half 1208 can also lock to one another via a locking mechanism (e.g., snap fit mechanism, magnetic mechanism, etc.).

In some examples, a support structure (not shown) or support pressure can be applied to an interior lumen of the catheter 232. In some examples, the support structure can be a rod or a guidewire sized such that the interior lumen is completely contacted by the rod or the guidewire. In other examples, a compressor can provide a pressure to the interior lumen. The support structure or support pressure can ensure that the catheter 232 does not collapse. Further, the support structure or support pressure can ensure that the softened material is fully smoothed out by allowing any indents in the catheter 232 to be filled, thereby allowing the catheter 232 to have a uniform and consistent diameter after reforming.

FIG. 13 is a block diagram of an exemplary controller 1300. Controller 1300 is configured to perform processing of data and communicate with the sensors 1360, motors for actuating components (e.g., clamp assemblies 106, 108, wheel assemblies 110, 112, etc.), and the heat device 114. In operation, controller 1300 communicates with one or more of the above-discussed components and may also be configured to communication with remote devices/systems.

As shown, controller 1300 includes hardware and software components such as network interfaces 1310, at least one processor 1320, sensors 1360 (e.g., sensors for determining position of components, power delivered to motors, etc.) and a memory 1340 interconnected by a system bus 1350. Network interface(s) 1310 can include mechanical, electrical, and signaling circuitry for communicating data over communication links, which may include wired or wireless communication links.

Network interfaces 1310 are configured to transmit and/or receive data using a variety of different communication protocols.

Processor 1320 represents a digital signal processor (e.g., a microprocessor, a microcontroller, or a fixed-logic processor, etc.) configured to execute instructions or logic to perform tasks for operation of the catheter restoration system 100. Processor 1320 may include a general purpose processor, special-purpose processor (where software instructions are incorporated into the processor), a state machine, application specific integrated circuit (ASIC), a programmable gate array (PGA), an individual component, a distributed group of processors, and the like. Processor 1320 typically operates in conjunction with shared or dedicated hardware, including but not limited to, hardware capable of executing software and hardware. For example, processor 1320 may include elements or logic adapted to execute software programs and manipulate data structures 1345, which may reside in memory 1340.

Sensors 1360, which may include sensors for positioning and operation of various components disclosed herein, typically operate in conjunction with processor 1320 to perform measurements, and can include special-purpose processors, detectors, transmitters, receivers, and the like. In this fashion, sensors 1360 may include hardware/software for generating, transmitting, receiving, detection, logging, and/or sampling various parameters of the catheter restoration system 100.

Memory 1340 comprises a plurality of storage locations that are addressable by processor 1320 for storing software programs and data structures 1345 associated with the embodiments described herein. An operating system 1342, portions of which may be typically resident in memory 1340 and executed by processor 1320, functionally organizes the device by, inter alia, invoking operations in support of software processes and/or services 1344 executing on controller 1300. These software processes and/or services 1344 may perform processing of data and communication with controller 1300, as described herein. Note that while process/service 1344 is shown in centralized memory 1340, some examples provide for these processes/services to be operated in a distributed computing network.

It will be apparent to those skilled in the art that other processor and memory types, including various computer-readable media, may be used to store and execute program instructions pertaining to functions of the catheter restoration system 100 described herein. Also, while the description illustrates various processes, it is expressly contemplated that various processes may be embodied as modules having portions of the process/service 1344 encoded thereon. In this fashion, the program modules may be encoded in one or more tangible computer readable storage media for execution, such as with fixed logic or programmable logic (e.g., software/computer instructions executed by a processor, and any processor may be a programmable processor, programmable digital logic such as field programmable gate arrays or an ASIC that comprises fixed digital logic. In general, any process logic may be embodied in processor 1320 or computer readable medium encoded with instructions for execution by processor 1320 that, when executed by the processor 1320, are operable to cause the processor 1320 to perform the functions described herein.

Further provided herein are methods for reforming and/or restoring a catheter of a medical device. The methods can be performed using the systems described herein. FIG. 14 illustrates a flow chart of a method 1400 for removing a kink from a catheter of a medical device and/or reforming a catheter of a medical device. In some examples, the method can begin by cleaning the catheter restoration system and all of the components described herein.

The method 1400 can then include determining the type of catheter (e.g., French size (diameter) of the catheter) to be reformed. Based on the type of catheter, wheels can be selected and secured to the catheter restoration system with a groove size corresponding to the diameter of the catheter to be reformed. Securing the wheels to a wheel assembly of the catheter restoration system can include placing an upper wheel in an upper housing and inserting a rod through the upper housing and a hole in the upper wheel, thereby securing the upper wheel to the upper housing. The lower wheel can similarly be secured to the lower housing by inserting a rod through the lower housing and a hole in the lower wheel. If two wheel assemblies are desired, similar steps can be taken to secure a second upper wheel and a second lower wheel to a second wheel assembly. In some examples, the rods can have threads that screw into corresponding holes in the upper housing and lower housing, thereby locking the wheels within the housings such that the wheels can only rotate about the rod and not translate in any direction.

The method 1400 can further include sliding the medical device tray, the first clamp (e.g., first clamp assembly), and second clamp (e.g., second clamp assembly) along the at least one guide rail to ensure that the system is able to slide properly. The method 1400 can further including warming up the heating device.

At block 1402, the method 1400 can include placing a body (e.g., handle) of the medical device in a medical device tray of a catheter restoration system. The method 1400 can then include aligning the kinked or damaged portion of a catheter of the medical device with a heat device having a nozzle and a thermal element. If the kinked or damaged portion is close to a body (e.g., handle) of the medical device, a body support (e.g., handle support) can be placed on the medical device tray to better align the kinked or damaged portion of the catheter with the nozzle of the heat device. For example, the body support can be used to move the plane of the catheter closer to the first clamp (e.g., first clamp assembly), as described herein.

In some examples, if the kinked or damaged portion of the catheter cannot be aligned with the nozzle of the heat device, medical device body can be removed from the medical device tray and inserted in a reverse tray on the opposite side of the catheter restoration system from the medical device tray. In some examples, the reverse tray allows for the kinked or damaged portion of the catheter to be aligned with the nozzle of the heat device.

Once the kinked or damaged portion is aligned with the nozzle of the heat device, the catheter can be rotated such that the wider sides of the kinked or damaged portion faces directly upward or downward (e.g., is perpendicular to the nozzle of the heat device).

At block 1404, the method 1400 can include securing a catheter of the medical device to one or more clamps (e.g., clamp assemblies). The kinked or damaged portion of the catheter can be between a first clamp assembly and a second clamp assembly operable to secure the catheter. Securing the catheter to the one or more clamps can include securing the catheter to a first clamp (e.g., first clamp assembly). The first clamp assembly can have a moveable portion and a fixed portion. The catheter can be placed in a gap between the moveable portion and the fixed portion while a toggle component is in an unlocked position. The toggle component can then be actuated to a locked position. Actuating the toggle component to the locked position can move the moveable portion towards the fixed portion, thereby exerting a force on the catheter and locking the catheter in place. The catheter can then be pulled at a second clamp assembly to ensure tension on the kinked or damaged portion of the catheter. The catheter can be placed in a gap between a moveable portion and fixed portion of the second clamp assembly when a toggle clamp is in an unlocked position. The toggle component can then be actuated to a locked position. Actuating the toggle component to the locked position can move the moveable portion of the second clamp assembly towards the fixed portion, thereby exerting a force on the catheter and locking the catheter in place. Once the catheter is locked in the first clamp assembly and the second clamp assembly with the kinked or damaged portion aligned with the nozzle of the heat device between the clamp assemblies, the catheter has been properly secured.

The method 1400 can further include lowering an upper wheel of the wheel assembly and aligning the groove of the upper wheel with the catheter. The wheel assembly is located between the first clamp assembly and the second clamp assembly. The upper wheel can be lowered manually, using a toggle clamp to lock and unlock the position of the upper wheel housing, and thereby the upper wheel, along an upper wheel guide rail, as described herein. In other examples, the upper wheel can be lowered electronically using a controller or processor as described herein. Once the groove of the upper wheel and the groove of the lower wheel align with the catheter, the catheter is ready to be provided heated air or gas from the heat device.

At block 1406, the method 1400 can include providing heated air or gas to the kinked or damaged portion of the catheter via the heating device.

The nozzle can provide the heated air or gas to the catheter. The heat device can be configured to provide the heated air or gas for a heating duration sufficient to soften the material of the catheter at the kinked or damaged portion. In some examples, the heating duration can be about 1 second to about 2 seconds, about 2 seconds to about 3 seconds, about 3 seconds to about 4 seconds, about 4 seconds to about 5 seconds, about 5 seconds to about 6 seconds, about 6 seconds to about 7 seconds, about 7 seconds to about 8 seconds, about 8 seconds to about 9 seconds, about 9 seconds to about 10 seconds, or more. In some examples, the heating duration can be about 1 second to about 5 seconds, about 5 seconds to about 10 seconds, about 10 seconds to about 15 seconds, about 15 seconds to about 20 seconds, about 20 seconds to about 25 seconds, about 25 seconds to about 30 seconds, about 30 seconds to about 35 seconds, about 35 seconds to about 40 seconds, about 40 seconds to about 45 seconds, about 45 seconds to about 50 seconds, about 50 seconds to about 55 seconds, about 55 seconds to about 1 minute, or more.

The thermal element of the heating device can heat the air or gas to a temperature of about 50 degrees Celsius (C) to about 55 degrees C., about 55 degrees C. to about 60 degrees C., about 60 degrees C. to about 65 degrees C., about 65 degrees C. to about 70 degrees C., about 70 degrees C. to about 75 degrees C., about 75 degrees C. to about 80 degrees C., about 80 degrees C. to about 85 degrees C., about 85 degrees C. to about 90 degrees C., about 90 degrees C. to about 95 degrees C., about 95 degrees C. to about 100 degrees C., about 100 degrees C. to about 105 degrees C., about 105 degrees C. to about 110 degrees C., about 110 degrees C. to about 115 degrees C., about 115 degrees C. to about 120 degrees C., about 120 degrees C. to about 125 degrees C., about 125 degrees C. to about 130 degrees C., about 130 degrees C. to about 135 degrees C., about 135 degrees C. to about 140 degrees C., about 140 degrees C. to about 145 degrees C., about 145 degrees C. to about 150 degrees C., about 150 degrees C. to about 155 degrees C., about 155 degrees C. to about 160 degrees C., about 160 degrees C. to about 165 degrees C., about 165 degrees C. to about 170 degrees C., or any range therebetween. The heated air or gas can be operable to soften the material of the catheter at the kinked or damaged portion without melting the material.

The temperature and the heating duration of the heated air or gas can be determined based on the type of material the catheter is made of. Depending on the type of material a temperature and heating duration can be chosen such that the material softens but does not melt. In some examples, the temperature and duration of the heated air or gas can also depend on the diameter of the catheter.

At block 1410, the method 1400 can include receiving the catheter in a forming component of a reforming assembly. The reforming component of the reforming assembly can be operable to reform the softened material of the catheter to a desired diameter. The reforming component can have a diameter substantially equal to the desired diameter of the catheter. In some examples, the reforming component can be a pair of corresponding grooves in a circumference of corresponding rolling wheels. In some examples, the reforming component can be a hole formed by corresponding half-circles of a reforming split mold.

At block 1412, the method 1400 can include moving the catheter along a longitudinal axis through the reforming assembly, thereby reforming the catheter. In some examples, moving the catheter along the longitudinal axis through the reforming assembly can include rolling the softened material of the catheter through a pair of rolling wheels, thereby reforming the catheter. Each wheel of the pair of rolling wheels can have a groove that is aligned with the catheter. The grooves can be sized such that they reform the catheter to its intended diameter. Rolling the softened material through the pair of rolling wheels can include translating the catheter back and forth along the at least one guide rail. In some examples, rolling the softened material back and force through the grooves in the pair of wheels provides a force or pressure to the catheter, thereby forming a consistent and uniform diameter by removing any protrusions and filling any indents in the catheter. In some examples, the softened material can be rolled through the pair of rolling wheels by translating the catheter back and forth along the at least one guide rail manually by an operator using handles on the first clamp assembly and the second clamp assembly. In some examples, the catheter can be moved back and forth using a motor or actuator operable to slide the first clamp assembly and second clamp assembly along the at least one guide rail, thereby removing the need for an operator to manually slide the catheter back and forth. In some examples, the at least one guide rail can have end stops to limit the distance that the catheter moves back and forth, thereby ensuring that the kinked or damaged portion of the catheter is rolled through the pair of rolling wheels efficiently. In some examples, the catheter restoration system can include one or more markings to indicate to an operator how far to slide the catheter back and forth along the at least one guide rail.

In some examples, moving the catheter along a longitudinal axis of the reforming assembly can include translating the catheter back and forth through a hole formed by two corresponding half-circle holes of a reforming split mold. The hole formed by the two corresponding half-circle holes of the reforming split mold can have a diameter substantially equal to a desired diameter of the catheter, such that moving the catheter along the longitudinal axis provides a force or pressure to the catheter thereby removing any protrusions and filling any indents. By removing any protrusions and filling any indents, the catheter is reformed to a consistent and uniform diameter.

In some examples, the soften material is rolled through the pair of rolling wheels one time, two times, three times, four times, five times, six times, seven times, eight times, nine times, ten times, or more.

At block 1412, the method 1400 can further include cooling the catheter after the catheter has been reformed by the pair of rolling wheels. In some examples, cooling the catheter can include providing cool air to the catheter via a fan for a cooling duration. In other examples, cooling the catheter can include allowing the catheter to cool at room temperature for a cooling duration. The cooling duration can be about 1 minute to about 10 minutes, about 10 minutes to about 20 minutes, about 20 minutes to about 30 minutes, about 30 minutes to about 40 minutes, about 40 minutes to about 50 minutes, or about an hour. In many examples, providing cooling air with a fan can shorten the cooling duration to about 1 minute to about 5 minutes.

The method 1400 can further include visually inspecting the catheter.

Visually inspecting the catheter can include ensuring that the kinked portion or damaged portion of the catheter has been successfully reformed. In other words, visually inspecting the catheter includes ensuring the catheter is fully restored to a desired shape (e.g., diameter). In some examples, if the kinked or damaged portion of the catheter has not been successfully reformed, the method 1400 can be repeated. Further, if the catheter has a second kinked or damaged portion at another location along the length of the catheter, the method 1400 can be repeated for the second kinked or damaged portion.

The method 1400 can further include inspecting the catheter using one or more sensors. For example, proximity sensors, machine vision sensors, and other types of sensors operable to determine a diameter of a catheter can be used to ensure that the diameter of the catheter has been reformed to a desired diameter within desired tolerances. In some examples, the desired tolerances can be tolerances required for clinical use of the catheter in a patient.

The method 1400 can further include cleaning the medical device. Cleaning the medical device can include contacting the medical device with a cleaning solution such as isopropyl alcohol or other similar cleaning solutions. The method 1400 can further include sterilizing the medical device. Sterilizing the medical device can include dry heat methods, steam methods, radiation methods, ethylene oxide methods, vaporized hydrogen peroxide methods, and other sterilization methods.

The disclosures shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims.

What is claimed is:

1. A system for removing kinks in a catheter of a medical device and/or reforming the catheter of the medical device, the system comprising:

at least one clamp operable to secure the catheter;

a heat device operable to provide heat to the catheter secured by the at least one clamp;

a reforming assembly including a reforming component operable to receive the catheter of the medical device therein such that when the catheter moves in relation to the reforming assembly along a longitudinal axis, the reforming assembly reforms the catheter and/or removes the kinks from the catheter; and a medical device tray operable to hold the medical device, wherein the at least one clamp includes a first clamp and a second clamp operable to secure the catheter on opposite sides of the reforming assembly, and wherein the first clamp and the second clamp are operable to move the catheter back and forth along the longitudinal axis, and wherein the medical device tray is operable to move along the longitudinal axis in coordination with the first clamp and the second clamp.

2. The system of claim 1, wherein the reforming assembly includes at least one pair of rolling wheels, wherein the reforming component includes a groove formed along a circumference of each wheel of the at least one pair of rolling wheels.

3. The system of claim 2, wherein the grooves are operable to contact an exterior surface of the catheter and reform the exterior surface of the catheter.

4. The system of claim 2, wherein the at least one pair of rolling wheels includes a plurality of interchangeable pairs of rolling wheels, wherein each pair of the plurality of interchangeable pairs of rolling wheels has a different groove size.

5. The system of claim 4, wherein each pair of wheels of the plurality of interchangeable pairs of wheels has a marking indicating a size of the groove.

6. The system of claim 1, wherein the heat device is operable to provide heated air to the catheter at a temperature of about 55 degrees C. to about 170 degrees C.

7. The system of claim 6, wherein the heated air is operable to soften the catheter of the medical device.

8. The system of claim 1, the system further comprising at least one guide rail, wherein the at least one clamp is slidably coupled to the at least one guide rail.

9. The system of claim 1, wherein the first clamp and the second clamp are operable to secure the catheter such that there is tension in the catheter between the first clamp and the second clamp.

10. The system of claim 1, the system further comprising a processor and a display.

11. The system of claim 10, the processor configured to:

receive one or more inputs from an operator;

display one or more instructions to the operator via the display; and cause the heat device to provide heated air to the catheter.

12. The system of claim 11, wherein the one or more instructions are one or more of choose recipe, connect device, ensure correct device positioning, begin heating, begin rolling, cooling in progress, remove medical device, and confirm medical device restoration.

13. A method for reforming a catheter of a medical device, the method comprising:

placing a body of the medical device in a medical device tray;

securing the catheter to at least one clamp;

providing heated air to at least one kink in the catheter via a heat device, thereby softening a material of the catheter;

receiving the catheter in a reforming component of a reforming assembly; and moving the catheter in relation to the reforming assembly along a longitudinal axis, thereby reforming the catheter and/or removing kinks from the catheter, wherein the at least one clamp includes a first clamp and a second clamp operable to secure the catheter on opposite sides of the reforming assembly, wherein the first clamp and the second clamp are operable to move the catheter back and forth along the longitudinal axis, and wherein the medical device tray is operable to move along the longitudinal axis in coordination with the first clamp and the second clamp.

14. The method of claim 13, wherein the heated air has a temperature of about 55 degrees C. to about 170 degrees C.

15. The method of claim 14, wherein the heated air is provided for about 5 seconds to about 20 seconds.

16. The method of claim 13, the method further comprising inspecting the catheter.

17. The method of claim 16, the method further comprising repeating the method if the catheter is not fully restored to a desired shape.

18. The method of claim 13, the method further comprising sterilizing the medical device.

19. The method of claim 13, wherein the reforming assembly includes a pair of rolling wheels, wherein the reforming component includes a groove formed along a circumference of each wheel of the pair of rolling wheels.

20. The system of claim 1, wherein the heat device is operable to provide heat to the catheter between (1) the first clamp and the reforming assembly and/or (2) the second clamp and the reforming assembly.

21. The system of claim 2, wherein the at least one pair of wheels includes a pair of vertically aligned wheels.

22. The system of claim 5, wherein the size of the groove corresponds to an outer diameter of the catheter.

* * * * *